US011696919B2

(12) United States Patent
Crutchley et al.

(10) Patent No.: US 11,696,919 B2
(45) Date of Patent: Jul. 11, 2023

(54) TOPICAL COMPOSITION

(71) Applicant: MC2 Therapeutics Limited, Guildford (GB)

(72) Inventors: Nigel Crutchley, Guildford (GB); Michelle Georgiou, Guildford (GB); Stephen Lenon, Guildford (GB); Morten Praestegaard, Guildford (GB)

(73) Assignee: MC2 Therapeutics Limited, Guildford (GB)

( * ) Notice: Subject to any disclaimer, the term of this patent is extended or adjusted under 35 U.S.C. 154(b) by 0 days.

(21) Appl. No.: 16/982,281

(22) PCT Filed: Mar. 18, 2019

(86) PCT No.: PCT/EP2019/056735
§ 371 (c)(1),
(2) Date: Sep. 18, 2020

(87) PCT Pub. No.: WO2019/179958
PCT Pub. Date: Sep. 26, 2019

(65) Prior Publication Data
US 2021/0015831 A1   Jan. 21, 2021

(30) Foreign Application Priority Data
Mar. 19, 2018  (EP) ..................... 18162664

(51) Int. Cl.
| | | |
|---|---|---|
| A61K 31/4709 | (2006.01) | |
| A61K 9/06 | (2006.01) | |
| A61K 47/10 | (2017.01) | |
| A61K 47/12 | (2006.01) | |
| A61P 17/10 | (2006.01) | |
| A61P 17/00 | (2006.01) | |
| A61P 17/04 | (2006.01) | |
| A61P 31/04 | (2006.01) | |
| A61K 31/573 | (2006.01) | |
| A61K 9/00 | (2006.01) | |
| A61K 31/047 | (2006.01) | |
| A61K 31/085 | (2006.01) | |
| A61K 31/355 | (2006.01) | |
| A61K 47/44 | (2017.01) | |

(52) U.S. Cl.
CPC .......... *A61K 31/573* (2013.01); *A61K 9/0014* (2013.01); *A61K 31/047* (2013.01); *A61K 31/085* (2013.01); *A61K 31/355* (2013.01); *A61K 47/44* (2013.01)

(58) Field of Classification Search
None
See application file for complete search history.

(56) References Cited

U.S. PATENT DOCUMENTS

| | | |
|---|---|---|
| 4,486,333 A | 12/1984 | Sebba |
| 4,533,546 A | 8/1985 | Kishi et al. |
| 4,871,723 A | 10/1989 | Makino et al. |
| 4,900,552 A | 2/1990 | Sanvordeker et al. |
| 4,936,933 A | 6/1990 | Yabsley et al. |
| 4,944,938 A | 7/1990 | Potini |
| 4,999,198 A | 3/1991 | Barnett et al. |
| 5,185,150 A | 2/1993 | DeLuca et al. |
| 5,474,979 A | 12/1995 | Ding et al. |
| 5,549,888 A | 8/1996 | Venkateswaran |
| 5,573,757 A | 11/1996 | Riess et al. |
| 5,645,856 A | 7/1997 | Lacy et al. |
| 5,660,858 A | 8/1997 | Parikh et al. |
| 5,763,426 A | 6/1998 | Hansen et al. |
| 5,840,881 A | 11/1998 | Uda et al. |
| 5,952,383 A | 9/1999 | Metziger et al. |
| 5,955,097 A | 9/1999 | Tapolsky et al. |
| 5,990,100 A | 11/1999 | Rosenberg et al. |
| 6,096,338 A | 8/2000 | Lacy et al. |
| 6,165,479 A | 12/2000 | Wheeler |
| 6,200,581 B1 | 3/2001 | Lin et al. |
| 6,238,678 B1 | 5/2001 | Oblong et al. |
| 6,538,039 B2 | 3/2003 | Laurent |
| 6,562,370 B2 | 5/2003 | Luo et al. |
| 6,585,997 B2 | 7/2003 | Moro et al. |
| 6,599,527 B1 | 7/2003 | Leigh et al. |
| 6,753,013 B1 | 6/2004 | Didriksen et al. |
| 6,787,529 B2 | 9/2004 | Hoy et al. |
| 7,001,607 B1 | 2/2006 | Menz et al. |
| RE39,706 E | 6/2007 | Hansen et al. |
| 7,709,431 B2 | 5/2010 | Mercurio et al. |

(Continued)

FOREIGN PATENT DOCUMENTS

| | | |
|---|---|---|
| CN | 1351499 A | 5/2002 |
| CN | 1832731 A | 9/2006 |

(Continued)

OTHER PUBLICATIONS

Crutchley, "The Encapsulation of Oils and Oil Soluble Substances Within Polymer Films", PhD Thesis, The University of Leeds (2006).
First Examination Report from Indian Application No. 201947029785, dated Jan. 24, 2020.
First Examination Report from Indian Patent Application No. 201847040549, dated Nov. 25, 2019.
G. Godwin, Harry's Cosmeticology 7th Edition (1982).
Hicks, "Investigating the Generation, Characterisation Structure of Biliquid Foams", PhD Thesis, University of Bristol (2005).

(Continued)

*Primary Examiner* — Layla Soroush
(74) *Attorney, Agent, or Firm* — Merchant & Gould P.C.

(57) ABSTRACT

The present invention relates to a composition for topical application comprising a polyaphron dispersion, the polyaphron dispersion comprising a continuous aqueous phase and at least one discontinuous oil phase,
wherein the polyaphron dispersion comprises calcipotriol, betamethasone dipropionate, alpha-tocopherol and butylated hydroxyanisole, and
wherein the composition has a pH of 7.75±0.5.

11 Claims, 6 Drawing Sheets

(56) References Cited

U.S. PATENT DOCUMENTS

| | | |
|---|---|---|
| 8,008,356 B2 | 8/2011 | Childs |
| 8,263,580 B2 | 9/2012 | Buchta et al. |
| 8,298,515 B2 | 10/2012 | Buchta et al. |
| 8,501,712 B2 | 8/2013 | Baker et al. |
| 8,574,563 B2 | 11/2013 | Bachand et al. |
| 8,629,111 B2 | 1/2014 | Acheampong et al. |
| 8,629,128 B2 | 1/2014 | Buchta |
| 8,633,162 B2 | 1/2014 | Acheampong et al. |
| 8,642,556 B2 | 2/2014 | Acheampong et al. |
| 8,648,008 B2 | 2/2014 | Misra et al. |
| 9,549,896 B2 | 1/2017 | Crutchley |
| 9,610,245 B2 | 4/2017 | Steele |
| 10,154,959 B1 | 12/2018 | Steele |
| 10,265,265 B2 | 4/2019 | Wheeler |
| 11,065,195 B2 | 7/2021 | Wheeler |
| 2005/0001643 A1 | 1/2005 | Yoshida et al. |
| 2005/0002546 A1 | 1/2005 | Florent et al. |
| 2005/0020546 A1 | 1/2005 | Laidlaw et al. |
| 2005/0026877 A1 | 2/2005 | Chen et al. |
| 2005/0082515 A1 | 4/2005 | Masuichi et al. |
| 2005/0147658 A1 | 7/2005 | Tapolsky et al. |
| 2005/0232869 A1 | 10/2005 | Tamarkin et al. |
| 2005/0238676 A1 | 10/2005 | Gladman et al. |
| 2005/0249757 A1 | 11/2005 | Kannan et al. |
| 2005/0281749 A1 | 12/2005 | Willcox et al. |
| 2005/0281750 A1 | 12/2005 | Willcox et al. |
| 2005/0281754 A1 | 12/2005 | Willcox et al. |
| 2005/0281755 A1 | 12/2005 | Zarif et al. |
| 2005/0281848 A1 | 12/2005 | Zanutto et al. |
| 2005/0281850 A1 | 12/2005 | Zanutto et al. |
| 2005/0282788 A1 | 12/2005 | Zanutto et al. |
| 2005/0282792 A1 | 12/2005 | Andres |
| 2006/0147383 A1 | 7/2006 | Mallard et al. |
| 2006/0188576 A1 | 8/2006 | Takruri |
| 2006/0228408 A1 | 10/2006 | Charman et al. |
| 2006/0239947 A1 | 10/2006 | Dias et al. |
| 2006/0292080 A1 | 12/2006 | Abram et al. |
| 2007/0041910 A1 | 2/2007 | Pitre et al. |
| 2007/0048369 A1 | 3/2007 | Foreman et al. |
| 2007/0059346 A1 | 3/2007 | Maibach |
| 2007/0190088 A1 | 8/2007 | Childs et al. |
| 2007/0207192 A1 | 9/2007 | Holl et al. |
| 2007/0276004 A1 | 11/2007 | Hirsch et al. |
| 2008/0064669 A1 | 3/2008 | Cohen et al. |
| 2008/0207570 A1 | 8/2008 | Segura-Orsoni |
| 2008/0227759 A1 | 9/2008 | Wheeler et al. |
| 2008/0234239 A1 | 9/2008 | Wheeler et al. |
| 2008/0254105 A1 | 10/2008 | Tapolsky et al. |
| 2009/0113031 A1 | 4/2009 | Ruan et al. |
| 2009/0137523 A1 | 5/2009 | Shin et al. |
| 2009/0221625 A1 | 9/2009 | Hirsch et al. |
| 2010/0062975 A1 | 3/2010 | Houck |
| 2010/0279951 A1 | 11/2010 | Morgan et al. |
| 2010/0286101 A1 | 11/2010 | Carbol et al. |
| 2011/0201639 A1 | 8/2011 | Skak et al. |
| 2011/0305643 A1 | 12/2011 | Gurge et al. |
| 2012/0184511 A1 | 7/2012 | Goebel |
| 2013/0101525 A1 | 4/2013 | Buchta |
| 2016/0318955 A1 | 11/2016 | Akama |
| 2019/0060288 A1 | 2/2019 | Crutchley |
| 2019/0358151 A1 | 11/2019 | Wheeler et al. |

FOREIGN PATENT DOCUMENTS

| | | |
|---|---|---|
| CN | 101115487 A | 1/2008 |
| CN | 101505725 A | 8/2009 |
| CN | 108815174 A | 11/2018 |
| EA | 200600139 | 8/2006 |
| EP | 0474126 A1 | 3/1992 |
| EP | 0474517 A2 | 3/1992 |
| EP | 0679154 A1 | 11/1995 |
| EP | 0679392 A1 | 11/1995 |
| EP | 0799620 A1 | 10/1997 |
| EP | 0884995 A1 | 12/1998 |
| EP | 1039893 A1 | 10/2000 |
| EP | 1178808 A1 | 2/2002 |
| EP | 1093371 B1 | 5/2005 |
| EP | 1575542 A1 | 9/2005 |
| EP | 1641463 A1 | 4/2006 |
| EP | 1686972 A1 | 8/2006 |
| EP | 1758586 A1 | 3/2007 |
| EP | 1758587 A1 | 3/2007 |
| EP | 1758588 A1 | 3/2007 |
| EP | 1758589 A1 | 3/2007 |
| EP | 1758591 A1 | 3/2007 |
| EP | 1765356 A1 | 3/2007 |
| EP | 1771180 A1 | 4/2007 |
| EP | 1778185 A1 | 5/2007 |
| EP | 1331927 B1 | 12/2007 |
| EP | 1970047 A1 | 9/2008 |
| EP | 1970048 A1 | 9/2008 |
| EP | 1970049 A1 | 9/2008 |
| EP | 2308468 A1 | 4/2011 |
| EP | 2596788 A1 | 5/2013 |
| JP | 62135417 | 6/1987 |
| JP | 10-139669 | 5/1998 |
| JP | H10-508588 A | 8/1998 |
| JP | 2005325140 | 11/2005 |
| JP | 2006522059 A | 9/2006 |
| JP | 2013507337 A | 3/2013 |
| RU | 2238734 C2 | 10/2004 |
| RU | 2276177 | 9/2010 |
| RU | 2 452 488 C2 | 6/2012 |
| WO | 9531211 A1 | 11/1995 |
| WO | 9600074 A1 | 1/1996 |
| WO | 9625923 A1 | 8/1996 |
| WO | 97/32559 A1 | 9/1997 |
| WO | 9732559 A1 | 9/1997 |
| WO | 9955312 A2 | 11/1999 |
| WO | 0064450 A1 | 11/2000 |
| WO | 0162214 A1 | 8/2001 |
| WO | 0204570 A2 | 1/2002 |
| WO | 0234235 A1 | 5/2002 |
| WO | 03/064024 A1 | 8/2003 |
| WO | 2004041227 A1 | 5/2004 |
| WO | 2005001643 A2 | 1/2005 |
| WO | 2005011628 A2 | 2/2005 |
| WO | 2005011643 A1 | 2/2005 |
| WO | 2005016321 A1 | 2/2005 |
| WO | 2005061321 A2 | 7/2005 |
| WO | 2005/082515 A2 | 9/2005 |
| WO | 2005082515 A2 | 9/2005 |
| WO | 2006050836 A2 | 5/2006 |
| WO | 2006/062334 A1 | 6/2006 |
| WO | 2006/099390 A1 | 9/2006 |
| WO | 2006111426 A1 | 10/2006 |
| WO | 2008/110815 A1 | 9/2008 |
| WO | 2008/110826 A1 | 9/2008 |
| WO | 2008110815 A1 | 9/2008 |
| WO | 2009/001092 A1 | 12/2008 |
| WO | 2009/001099 A2 | 12/2008 |
| WO | 2009001099 A2 | 12/2008 |
| WO | 2009007409 A2 | 1/2009 |
| WO | 2009071594 A1 | 6/2009 |
| WO | 2009090495 A1 | 7/2009 |
| WO | 2010/096868 A1 | 9/2010 |
| WO | 2010120838 A1 | 10/2010 |
| WO | 2010124096 A1 | 10/2010 |
| WO | 2010141591 A1 | 12/2010 |
| WO | 2011/026076 A2 | 3/2011 |
| WO | 2011154004 A1 | 12/2011 |
| WO | 2012/011566 A1 | 1/2012 |
| WO | 2017/093857 A1 | 6/2017 |
| WO | 2017/203456 A1 | 11/2017 |

OTHER PUBLICATIONS

International Preliminary Report on Patenatbility for PCT/EP2017/057897, dated Oct. 9, 2018.

International Preliminary Report on Patenatbility for PCT/GB2018/050263 dated Aug. 15, 2019.

International Search Report and Written Opinion for PCT/EP2017/057897 dated Jun. 8, 2017.

(56) References Cited

OTHER PUBLICATIONS

International Search Report and Written Opinion for PCT/GB2018/050263 dated Apr. 9, 2018.
Jay Araman et al., "Topical Delivery ofErythromycin from Various Formulations: An In Vivo Hairless Mouse Study", Journal of Pharmaceutical Sciences (1996) vol. 85(10): 1082-1084.
L. Eichenfield, "Long-term safety of crisaborole topical ointment, 2%, in atopic dermatitis", Journal of Investigative Dermatology, vol. 136 (5): S49.
Lye and Stuckey, "Structure and stability of colloidal liquid aphrons," Colloid and Surfaces, 131, 119-136 (1998).
Mollison et al., "A macrolactam inhibitor of T helper type 1 and T helper type 2 cytokine biosynthesis for topical treatment of inflammatory skin diseases", J Invest Dermatol., 112(5):729-38 (1999).
Search Report for British Patent Application No. 1701583.5, dated Oct. 25, 2017.
Search Report for European Patent Application No. 16163724.4, dated Sep. 19, 2016.
Sebba, "Biliquid Foams—A Preliminary Report", J. Colloid and Interface Science, 40:2, 468-474 (1972).
Sebba, "The Behaviour of Minute Oil Droplets Encapsulated in a Water Film", Colloid Polymer Sciences, 257, 392-396 (1979).
T. Akama et al., "Discovery and structure-activity study of a novel benzoxaborole anti-inflammatory agent (AN2728) for the potential topical treatment of psoriasis and atopic dermatitis", Bioorganic & Medicinal Chemistry Letters vol. 19 (8) (2009).
Yamanaka et al., "Development and evaluation of a tacrolimus cream formulation using a binary solvent system", International Journal of Pharmaceuticals, (2014).
U.S. Appl. No. 16/090,993, filed Oct. 3, 2018.
U.S. Appl. No. 16/482,177, filed Jul. 30, 2019.
Allowed Claims for U.S. Appl. No. 16/287,779, filed Feb. 27, 2019 (Exhibit A).
Japanese Examination Report for JP Application No. 2019-502155 dated Mar. 23, 2021—English Translation provided (6 pages).
Indian Hearing Notice for IN Application No. 201847040549 mailed Sep. 9, 2021 (3 pages).
Chinese Examination Report for CN Application No. 201780026171.3 dated Jun. 28, 2021—English Translation provided (6 pages).
Remitz et al. "Tacrolimus ointment improves psoriasis in a microplaque assay." British Journal of Dermatology, vol. 141. (1999) pp. 103-107.
Chinese Patent Application No. 200880008496.X Office Action.
Russian Patent Application No. 2009138045 Office Action.
JP10-139669, 1988, (English translation of claims).
Chinese Office Action for CN Application No. 202110793951.9 dated Dec. 31, 2021 (15 pages, with English translation).
Animal Science and Technology College, "Progress in the Effects of Anise Oil on Animal Performance Health and Immune Function Shining," 2017, 5 pages (English abstract).
"Adams, "Vitamin D mythes, facts and statistics," Natural News, 2005, Abstract.".
"Ashcroft et al., "Systematic Review . . . Plaque Psoriasis" British Medical Journal, 320:963-967 (2000).".
"Office Action for Chinese Patent Application No. 200880008496.X (with English translation) (11 pages).".
"EP 11158099.9 Search Report dated Sep. 27, 2011.".
"Charakida et al., "Calcipotriolbetamethasone dipropionate for the treatment of psoriasis," Expert Opin. Pharmacother, 7(5):597-606 (2006)".
"EP Application No. 1196067.0 Ryttov Declaration (4 pages).".
"EP Application No. 11196069.6 Response filed Aug. 8, 2013 (93 pages).".
"Farines et al., "Analysis of the triglycerides of some vegetable oils," Journal of Chemical Education, 65(5):464-466 (1988).".
"Final Report on the safety assessmnet of peanut (*Arachis hypogaea*) oil etc. International Journal of Toxicology, 20 (2):65-77 (2001).".
"Guenther et al., "Efficacy and safety of a new combination of calcipotriol and betamethasone dipropionate (once or twice daily) compared to calcipotriol (twice daily) in the treatment of psoriasis vulgaris: a randomized, double-blind, vehicle-controlled clinical trial," British Journal of Dermatology, 147:316-323 (2002).".
"Kaufmann et al., "A New CalciptriolBetamethasone Dipropionate Formulation (DaivobetTM) is an Effective Once-Daily Treatment for Psoriasis vulgaris," Dermatology, 205:389-393 (2005).".
"Kim et al., "Lipolysis of Com, peanut and randomized peanut oils," Lipids, 18(11):842-844 (1983).".
"Kragballe, "Treatment of psoriasis with calcipotriol and other vitamin D analogues," Journal of the American Academy of Dermatology, Dec. 1992, vol. 27, Issue 6, part 1 (Abstract only).".
"Kragballe et al ., "Efficacy of once-daily treatment regimens wit calcipotriolbetamethasone dipropionate ointment and calcipotriol ointment in psoriasis vulgaris," British Journal of Dermatology, 150:1167-1173 (2004).".
"Lebwohl, "The Evolution ofVitamin D Analogues for the Treatment of Psoriasis," Arch. Dermatol., 131:1323-1324 (1995).".
"Montalto, Jr., "A Study of the Feasibility of Polyaphrons as Trasdermal Drug Delivery Systems," MS thesis; University of Rhode Island, Kingston, 1984, Print (95 pages).".
"Ortonne et al., "Efficacy of treatment with calcipotriolbetamethasone dipropionate followed by calcipotriol alone compared with tacalcitol for the treatment of psoriasis vaulgaris: a randomized, doubl-blind trial," Dermatology, 2004209(4):308-313 (2004) PMID U.S. Appl. No. 15/539,894, Medline, DA 2004-11-12.".
"PCT/EP2012/054498 International Search Report dated May 7, 2012.".
"PCT/GB2004/003329 International Search Report dated Feb. 16, 2005.".
"Poyner et al., "Long Term Treatment of Chronic Plaque Psoriasis with Calcipotriol" Journal of Dermatological freatment, 4(4):173-177 (1993).".
"Russian Patent Application No. 2009138045 Office Action (with English translation).".
"Sebba, "Preparation and Properties of Polyaphrons (Biliquid Foams)" Chemistry and Industry, Chemical Society, Letchworth, GB, No. 10,1984, pp. 367-372.".
"Traulsen et al., "The Atrophogenic Potential and Dermal Tolerance of CalcipotriolBetamethasone Dipropionate Ointment Compared with Betamethasone Dipropionate Ointment," Dermatology, 207:166-172 (2003).".
"U.S. Office Action cited in U.S. Appl. No. 14/003,871 dated Jun. 24, 2015.".
"U.S. Office Action cited in U.S. Appl. No. 12/450,183 dated Aug. 26, 2015.".
"Van De Kerkhol et al., "A two-compound product containing calcipotriol and betamethasone dipropionate provides rapid, effective treatment of psoriasis vulgaris regardless of baseline disease severity", Dermatology, 210(4):294-299 (2005) (Abstract).".
"Van De Kerkhol et al., "Mixed treatment comparison of a two-compound formulation (TCF) product containing calcipotriol and betamethasone dipropionate with other topical treatments in psoriasis vulgaris," Current Medical Research & Opinion, 27(1):225-238 (2011).".
"Wheeler, "High Internal Phase Dispersions," Conference: Cosmetics and Coloids (online) Feb. 15, 2005, pp. 1-12.".
"CapricCaprylic Triglyceride vs. Fractionated Coconut Oil, from http:chemicaloftheday.squarespace.comqa201528capriccaprylic-triglyceride-vs-fractionated-coconut-oil.html, pp. 1-6, accessed Jun. 12, 2015".
"Gelatine, from http:www.gelita.comsolutions-and-productsgelatine-gelling-agent-numerous-applications, p. 1, accessed Jun. 13, 2015".
"Eyedrops Medical Definition, from http:www.merriam-webster.commedicaleyedrops, p. 1, accessed Dec. 24, 2015".
"Decision of Court of Appeals for Federal circuit, Leo Pharmaceutical Products, Ltd . Appelle, 2012-1520, Appeal from BPAI No. 95/000,153, decided Aug. 12, 2013".
"Le Yan (Stability, Transport, And Applications of polyaphrons in poromedia, A dissertation Submitted to the Graduate Faculty of the Louisianna State University and Agricultural and Mechanical College in Partial fulfillment of the Requirements for the degree of Doctor of Philosophy, May 2005)".

(56) References Cited

OTHER PUBLICATIONS

"Rathore et al., An Insight into Ophthalmic Drug Delivery System, International Journal of Pharmaceutical Sciences and Drug Research, 2009, pp. 1-5".

"Patel et al., Ophthalmic Drug Delivery System—A Review, Der Pharmacia Lettre, 2010, 2, pp. 100-115, published Feb. 4, 2010".

"Lye et al. "Immobilization of Candida cylindracea Lipase on Colloidal Liquid Aphrons (CLAs) and Development of a ContinuoCLA-Membrane Reactor," Biotechnology and Bioengineering, vol. 51, pp. 69-78 (1996)".

Stuckey et al. "The Immobilisation of Enzymes on Colloidal Liquid Aphrons (CLAs) for Bi-phasic Reactions: Stability, Protein Structure, and use in Crossflow Membrane Bioreactors".

"T.J. Lin: "Surfactant Location and Required HLB"; J. Soc. Cosmet. Chem., 21 (1970), pp. 365-375".

International Search Report and Written Opinion for International Application No. PCT/EP2019/056735, dated May 29, 2019.

S.E. Wolverton, Comprehensive Dermatologic Drug Therapy 3rd Edition (2012), p. 13.

Office Action for Russian Patent Application No. 2020133965/04(062226) dated Sep. 12, 2022, 4 pages.

Search Report for Russian Patent Application No. 2020133965/04(062226) dated Sep. 12, 2022, 23 pages.

Housam Haj Hamdo, et al. "Synergistic Effect of combined some natural and synthetic antioxidants to increase oxidative stability using DPPH test", International Journal of ChemTech Research, 2014, 6(4):2539-2545, USA (7 Pages).

Kaseigaku Zasshi, "Deterioration of Oils contained in fried Foods during the Storate", Home finance Magazines, 1969, 20(2):90-94 (5 pages).

Regine Kahl, et al. "Toxicology of the synthetic antioxidants BhA and BHT in comparison wiht the natural antioxidant vitamin E", Z Lebensm Unters Forsch, 1993, 196:329-338 (English Abstract included on first page).

TOPICAL COMPOSITION

This application is a National Stage Application of International Application No. PCT/EP2019/056735, filed 18 Mar. 2019, which claims benefit of Ser. No. 18/162,664.9, filed Mar. 19, 2018 in Europe and which applications are incorporated herein by reference. To the extent appropriate, a claim of priority is made to each of the above disclosed applications.

The present invention relates to a topical composition. In particular, the invention relates to a topical composition comprising calcipotriol and betamethasone dipropionate. The composition has improved chemical stability, skin permeation, aesthetics and/or patient compliance compared to existing compositions comprising calcipotriol and betamethasone dipropionate.

It is known for topical formulations comprising calcipotriol and betamethasone dipropionate to be used for the treatment of psoriasis. Traditionally, topical formulations in which both components are stable have proved challenging to manufacture. This is because the two compounds are stable at different pH values. In particular, calcipotriol requires a pH value above 8 for maximum stability, whereas betamethasone (9-fluoro-11,17,21-trihydroxy-16-methyl-pregna-1,4-diene-3,20-dione) and esters thereof require pH values in the range 4 to 6 for maximum stability. It is therefore difficult to combine the two active components in a single formulation while maintaining good stability of the active compounds if water is present in the formulation.

One approach to achieve stability of the two actives is to formulate them in a composition that does not contain water. This approach has been followed in the development of three commercially available products: Daivobet® ointment, Daivobet® gel and Enstilar® foam. The absence of water limits chemical degradation due to hydrolysis or pH incompatibility and the occlusive nature of the bulk of the excipients creates a high degree of occlusion aiding permeation of the actives. However, like most ointments and oil-based formulations, the lack of water and the presence of paraffin and wax components give the formulations a poor aesthetic profile (S. E. Wolverton, Comprehensive Dermatologic Drug Therapy 3rd Edition (2012), p13). The poor aesthetic profile can limit patient compliance.

In WO 2008/110815, the problem of pH incompatibility of calcipotriol and betamethasone dipropionate is overcome by incorporating them into a composition comprising a polyaphron dispersion. Because the compositions include water, they can be formulated into creams, which have a better aesthetic profile than non-aqueous ointments and gels such as the Daivobet® products discussed above. This, in turn, can elicit improved patient compliance.

Nevertheless, while the Examples of WO 2008/110815 exhibit good chemical stability, the present inventors have found that the chemical stability can be improved as described herein.

There is a need to formulate an improved composition suitable for topical application which addresses at least some of the problems of the compositions of the prior art.

Accordingly, it is one object of the present invention to provide a formulation comprising calcipotriol and betamethasone dipropionate having better aesthetics than prior art non-aqueous formulations such as Daivobet® ointment, Daivobet® gel and Enstilar® foam.

It is an alternative and/or additional aspect of the present invention to provide a formulation comprising calcipotriol and betamethasone dipropionate that can elicit better patient compliance than prior art non-aqueous formulations such as Daivobet® ointment, Daivobet® gel and Enstilar® foam.

It is an alternative and/or additional aspect of the present invention to provide a formulation comprising calcipotriol and betamethasone dipropionate having improved chemical stability compared to existing cream formulations, such as those disclosed in WO 2008/110815.

It is an alternative and/or additional aspect of the present invention to provide a formulation comprising calcipotriol and betamethasone dipropionate having better skin permeation than prior art non-aqueous formulations such as Daivobet® ointment, Daivobet® gel and Enstilar® foam and/or existing cream formulations, such as those disclosed in WO 2008/110815.

According to a first aspect, the present invention provides a composition for topical application comprising a polyaphron dispersion, the polyaphron dispersion comprising a continuous aqueous phase and at least one discontinuous oil phase,
wherein the polyaphron dispersion comprises calcipotriol, betamethasone dipropionate, alpha-tocopherol and butylated hydroxyanisole, and
wherein the composition has a pH of 7.75±0.5.

The present inventors have surprisingly found that a specific combination of antioxidants, alpha-tocopherol and butylated hydroxyanisole, interact to provide significantly enhanced calcipotriol chemical stability when the pH of the composition is within the range of 7.75±0.5. This phenomenon was not observed when other combinations of antioxidants were tested.

The present invention will now be described further. In the following passages different aspects/embodiments of the invention are defined in more detail. Each aspect/embodiment so defined may be combined with any other aspect/embodiment or aspects/embodiments unless clearly indicated to the contrary. In particular, any feature indicated as being preferred or advantageous may be combined with any other feature or features indicated as being preferred or advantageous.

The present invention provides a composition for topical application. A composition for topical application is defined herein as a composition that is suitable for direct application to a part of the human or animal body. Preferably, the composition is suitable for direct application to the skin, for example the face, scalp, feet, limbs or trunk.

The composition of the present invention comprises a polyaphron dispersion. The term "polyaphron dispersion" as used in its general sense refers to a particular kind of hydrophilic liquid-in-hydrophobic liquid or hydrophobic liquid-in-hydrophilic liquid dispersion comprising (a) a hydrophilic liquid miscible phase, (b) a second hydrophobic phase being immiscible or substantially immiscible with the first phase and (c) one or more surfactants, wherein the dispersed or discontinuous phase is in the form of small (e.g. micron to sub-micron diameter, but more usually at least 1 micron diameter) droplets, and the whole having the following characteristics, which distinguish polyaphron dispersions from conventional or common emulsions and other dispersion types:

1. They are capable of existing in a stable form wherein the volume fraction of the dispersed phase ($\phi_{ip}$) is greater than 0.7 and can be as high as 0.97. ($\phi_{ip}$) is the volume ratio of discontinuous to continuous phase expressed as a fraction).
2. The microscopic appearance of polyaphron dispersions where $\phi_{ip}$ is greater than 0.7 is that of an aggregate of individual droplets, pushed closely together into polyhedral shapes, resembling the appearance of a gas foam. In this form, the dispersion has gel-like properties and is referred to as a Gel Polyaphron Dispersion (GPD).
3. Stable polyaphron dispersions can be formed with a surfactant concentration less than 3% and more typically less than 2% by weight of the total composition.
4. Gel Polyaphron Dispersions (as described in 2 above) can be diluted to any extent by the addition of more continuous phase without the addition of more surfactant, when the gel-like properties disappear. Once φ has been reduced to below 0.7, the individual droplets of internal phase become separated to take the form of spherical droplets, which remain stable and intact but which may nevertheless join together in loose associations and float to the top or sink to the bottom of the diluted dispersion (depending on the relative densities of the two phases). In this diluted form each droplet is referred to as a Colloidal Liquid Aphron (CLA). Simple shaking of the diluted dispersion instantly causes a homogeneous, stable dispersion of Colloidal Liquid Aphrons to re-form.

Each of the above characteristics and a combination of them clearly differentiate the polyaphron dispersions of the present invention from conventional emulsions and other dispersion types which do not have all of those characteristics. Polyaphron dispersions are disclosed in the following literature references by Sebba: "Biliquid Foams", J. Colloid and Interface Science, 40 (1972) 468-474 and "The Behaviour of Minute Oil Droplets Encapsulated in a Water Film", Colloid Polymer Sciences, 257 (1979) 392-396, Hicks "Investigating the Generation, Characterisation, and Structure of Biliquid Foams", PhD Thesis, University of Bristol, 2005, Crutchley "The Encapsulation of Oils and Oil Soluble Substances Within Polymer Films", PhD Thesis, The University of Leeds, 2006 and Lye and Stuckey, Colloid and Surfaces, 131 (1998) 119-136. Aphrons are also disclosed in U.S. Pat. No. 4,486,333 and WO 97/32559.

Polyaphron dispersions are sometimes referred to as 'Biliquid Foams', 'High Internal Phase Emulsions (HIPEs)', 'High Internal Phase Ratio Emulsions (HIPREs)' and 'Gel Emulsions'. In U.S. Pat. No. 5,573,757 a composition comprising a polyaphron dispersion is described as "a viscoelastic gel". All descriptions that refer to dispersions having the characteristics described above are polyaphron dispersions as used in the present invention.

The polyaphron dispersion comprises a continuous aqueous phase and at least one discontinuous oil phase. In other words, the polyaphron dispersion comprises a dispersion of at least one discontinuous oil phase in a continuous aqueous phase. As noted above, in a polyaphron dispersion, the discontinuous phase is in the form of small droplets. Thus, the term "discontinuous phase" as used herein refers to the plurality of oil droplets that form that particular oil phase. It is not used to refer to a single oil droplet. The continuous phase is physically distinct from the discontinuous oil phase(s).

The inclusion of a continuous aqueous phase in the present composition enables it to be provided in the form of a lotion or cream, as opposed to an ointment. Thus, the present composition has an improved aesthetic profile relative to the ointments of the prior art, thereby improving patient compliance. Preferably, the composition is in the form of a lotion, cream or spray, most preferably a cream.

It will be understood that each of the at least one discontinuous phases comprises a pharmaceutically acceptable oil. Examples of pharmaceutically acceptable oils which may be used in the present invention include coconut oil, squalane, isopropyl myristate, isopropyl isostearate, isopropyl palmitate, modified triglycerides, caprylic capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl trilinoleate, glyceryl trilinolenate, glyceryl trioleate, glyceryl triundecanoate, linoleic glycerides, saturated polyglycolized glycerides, synthetic medium chain triglyceride containing primarily $C_8$-$C_{12}$ fatty acid chains, medium chain triglycerides, long chain triglycerides, modified triglycerides, fractionated triglycerides, isostearyl isostearate, diisopropyl adipate, mineral oil, dimethicone, cyclomethicone, hydrogenated polyisobutene, heptamethylnonane, and mixtures thereof.

Preferably, the composition does not comprise a wax component that is solid at 25° C. Preferably, at least one of said discontinuous oil phase(s) comprises caprilic capric triglycerides (CCT) and isopropyl myristate (IPM). Preferably, the caprilic capric triglycerides are present in a total amount of from 2 to 12 wt % by weight of the composition, more preferably from 4 to 10 wt %, and most preferably from 5 to 8 wt %. Preferably, the isopropyl myristate is present in a total amount of from 30 to 50 wt %, more preferably from 35 to 45 wt % and most preferably from 37 to 43 wt %. Preferably, the isopropyl myristate and caprilic capric triglycerides are present in a weight ratio of from 3:1 to 12:1, more preferably from 4:1 to 8:1. The present inventors have found that blending a small amount of CCT into at least one discontinuous phase gives rise to improved dermal diffusion of the betamethasone dipropionate and calcipotriol compared to when IPM is used alone. This is surprising because IPM is a known permeation enhancer and IPM alone would be expected to give better diffusion of the actives than a combination of CCT and IPM. It has been found that the improved active diffusion is only obtained when the CCT and IPM are present in the above (relative) amounts; including too much CCT has been found to have a negative impact on dermal diffusion of the actives.

Preferably, the at least one discontinuous oil phase is present in a total amount from 10 to 90 wt % by weight of the composition, more preferably from 40 to 90 wt %. Preferably, the at least one discontinuous oil phase is present in a total amount of from 65 to 80 wt % by weight of the composition, more preferably from 70 to 75 wt %. Alternatively, the composition may comprise a lower amount of discontinuous oil phase. For example, the at least one discontinuous oil phase may be present in a total amount of less than 70 wt % by weight of the composition, more preferably from 50 to 70 wt %. These lower amounts of discontinuous oil phase are typical for scalp products.

The polyaphron dispersion comprises calcipotriol. Calcipotriol is a vitamin D analogue known for use in the treatment of psoriasis. Its chemical formula is shown in FIG. 1. The source of calcipotriol used in the present invention is preferably anhydrous calcipotriol or calcipotriol hydrate, although it will be appreciated that other sources of calcipotriol may be used, such as salts and solvates thereof. However, the amounts of calcipotriol to be incorporated into the compositions described herein are based on the anhydrous form of calcipotriol (that is, based on the molecular weight of the chemical formula shown in FIG. 1).

The polyaphron dispersion comprises betamethasone dipropionate. Betamethasone dipropionate is an ester of betamethasone, known for use in combination with calcipotriol in the treatment of psoriasis. The chemical formula of betamethasone dipropionate is shown in FIG. 2. The source of betamethasone dipropionate used in the present invention is preferably anhydrous betamethasone dipropionate, although it will be appreciated that other sources of betamethasone dipropionate may be used, such as salts, hydrates and solvates thereof. However, the amounts of betamethasone dipropionate to be incorporated into the compositions described herein are based on the anhydrous form of betamethasone dipropionate (that is, based on the molecular weight of the chemical formula shown in FIG. 2).

It would be within the capabilities of the skilled person to adjust the quantities of the source of calcipotriol and the source of betamethasone dipropionate used in the preparation of the composition depending on the respective sources used to provide the desired respective amounts in the final composition.

The composition of the present invention has a pH of 7.75±0.5. Preferably, the composition has a pH of 7.75±0.25. It will be understood that any suitable acid or base may be used to adjust the pH to the appropriate value or pH range. Advantageously and preferably, the pH of the composition may be stabilised by the incorporation of a suitable buffer into the continuous aqueous phase. Suitable buffer systems having a pH within the specified range will be familiar to those skilled in the art.

Surprisingly and unexpectedly, the present inventors have discovered that two specific antioxidants, butylated hydroxyanisole and alpha-tocopherol, interact within the pH range of 7.75±0.5 to provide significantly enhanced calcipotriol chemical stability. In particular, while butylated hydroxyanisole alone and alpha-tocopherol alone had no significant effect on the calcipotriol stability relative to the control (in which no antioxidant was used), the combination of the two antioxidants together dramatically improved the calcipotriol stability, and thereby the overall chemical stability of the composition. This phenomenon was not observed for other combinations of antioxidants.

Thus, the polyaphron dispersion comprises alpha-tocopherol and butylated hydroxyanisole. Including these antioxidants allows for a composition that is chemically stable based on the definition provided herein. The term "alpha-tocopherol" encompasses all stereoisomers. Thus, the alpha-tocopherol can be RRR-alpha-tocopherol. Alternatively, the alpha-tocopherol can be a mixture of stereoisomers such as all-rac-alpha-tocopherol. The source of alpha-tocopherol used in the present invention can be anhydrous alpha-tocopherol, or salts, hydrates, solvates or esters thereof, such as alpha-tocopheryl acetate. The most preferred source of alpha-tocopherol is anhydrous alpha-tocopherol. Butylated hydroxyanisole is typically prepared from 4-methoxyphenol and isobutylene and is typically a mixture of 2-tert-butyl-4-hydroxyanisole and 3-tert-butyl-4-hydroxyanisole isomers. Alternatively, one of the isomers can be used in isolation. The source of butylated hydroxyanisole used in the present invention can be anhydrous butylated hydroxyanisole, or salts, hydrates, solvates or esters thereof. The most preferred source butylated hydroxyanisole is anhydrous butylated hydroxyanisole.

The polyaphron dispersion may further comprise isomers of tocopherol other than alpha-tocopherol. In particular, the polyaphron dispersion may comprise beta-tocopherol, gamma-tocopherol and/or delta-tocopherol. In these embodiments, the beta-tocopherol, gamma-tocopherol and/or delta-tocopherol are preferably present in a total amount of at most 100 wt % by weight of the alpha-tocopherol, more preferably at most 50 wt %, still more preferably at most 30 wt %, still more preferably at most 20 wt %, and most preferably at most 10 wt %.

Preferably, the composition is chemically stable for at least 6 months at 25° C.±2° C., as measured at 60% RH±5%. Preferably, the composition is chemically stable for at least 12 months at 5° C.±3° C., as measured at 60% RH±5%. The chemical stability is preferably measured after storage of the composition in a closed, airtight amber glass container with headspace comprising no more than 5% by volume of the total usable volume of the container. The container is preferably sealed without having been sparged with nitrogen. By "chemically stable" it is meant that the individual amounts of 24-epi-calcipotriol and 5,6-trans-calcipotriol increase by less than 1 wt % by weight of the calcipotriol compared to t=0, and/or that the individual amounts of betamethasone-17-propionate, betamethasone-21-propionate and betamethasone-21-acetate-17-propionate increase by less than 1 wt % by weight of the betamethasone dipropionate at compared to t=0. The impurities listed above are the known major degradation products of calcipotriol and betamethasone dipropionate in aqueous media.

Preferably the amount of each impurity is calculated by measuring the area of the impurity peak in an HPLC chromatogram compared to the total area of all the peaks associated with the relevant API in the chromatogram, expressed as a percentage.

Preferably, the composition is physically stable for at least 6 months at 25° C.±2° C., as measured at 60% RH±5%. Preferably, the composition is physically stable for at least 12 months at 5° C.±3° C., as measured at 60% RH±5%. The physical stability is preferably measured after storage of the composition in a closed, airtight amber glass container with headspace comprising no more than 5% by volume of the total usable volume of the container. The container is preferably sealed without having been sparged with nitrogen. By "physically stable" it is meant that the composition appears as a homogeneous cream with no gross apparent rheological or appearance changes compared to t=0.

Preferably, the continuous aqueous phase comprises at least 10 wt % water by weight of the composition, more preferably from 10 to 30 wt %, still more preferably from 15 to 25 wt %, and most preferably from 18 to 22 wt %. Alternatively, the composition may comprise a higher amount of water. For example, the continuous aqueous phase may comprise at least 30 wt % water by weight of the composition, more preferably from 30 to 50 wt %. These higher amounts of water are typical for scalp products.

Preferably, the continuous aqueous phase comprises at least 0.5 wt % isopropanol by weight of the composition, more preferably at least 4 wt %, still more preferably from 4 to 10 wt %, and most preferably from 5 to 7 wt %. While it is generally desirable to limit the alcohol content of a topical composition owing to their drying effect on the skin, the present inventors have found that the presence of isopropanol in the continuous aqueous phase helps to improve the skin permeation of both of the actives. The isopropanol also contributes to formulation preservation.

Preferably, the continuous aqueous phase is present in a total amount of from 10 to 90 wt % by weight of the composition, more preferably from 10 to 60 wt %. Preferably, the continuous aqueous phase is present in an amount from 20 to 35 wt % by weight of the composition, most preferably from 25 to 30 wt %. Alternatively, the composition may comprise a higher amount of continuous phase. For example, the continuous aqueous phase may be present in an amount of at least 30 wt % by weight of the composition, more preferably from 30 to 50 wt %. These higher amounts of continuous aqueous phase are typical for scalp products.

Preferably, the composition comprises from 0.001 to 0.01 wt % calcipotriol by weight of the composition, more preferably from 0.002 to 0.008 wt %, and most preferably from 0.004 to 0.006 wt %. Preferably, the calcipotriol is predominantly in at least one of the discontinuous oil phase(s). By predominantly in at least one of the discontinuous oil phase(s) it is meant that at least 60 wt % of the calcipotriol is in at least one of the discontinuous oil phase(s), preferably at least 70 wt %, and most preferably at least 80 wt %. Preferably, at most 99 wt % of the calcipotriol is in at least one of the discontinuous oil phase(s).

Preferably, the composition comprises from 0.02 to 0.1 wt % betamethasone dipropionate by weight of the composition, more preferably from 0.04 to 0.08 wt %, and most preferably from 0.05 to 0.07 wt %. Preferably, the betamethasone dipropionate is predominantly in at least one of the discontinuous oil phase(s). By predominantly in at least one of the discontinuous oil phase(s) it is meant that at least 60 wt % of the betamethasone dipropionate is in at least one of the discontinuous oil phase(s), preferably at least 70 wt %, and most preferably at least 80 wt %. Preferably, at most 99 wt % of the betamethasone dipropionate is in at least one of the discontinuous oil phase(s).

Preferably, the composition comprises from 0.001 to 0.005 wt % alpha-tocopherol by weight of the composition, more preferably from 0.0015 to 0.003 wt %, and most preferably about 0.002 wt %. Preferably, the alpha-tocopherol is predominantly in at least one of the discontinuous oil phase(s). By predominantly in at least one of the discontinuous oil phase(s) it is meant that at least 60 wt % of the alpha-tocopherol is in at least one of the discontinuous oil phase(s), preferably at least 70 wt %, and most preferably at least 80 wt %. Preferably, at most 99 wt % of the alpha-tocopherol is in at least one of the discontinuous oil phase(s).

Preferably, the composition comprises from 0.05 to 0.5 wt % butylated hydroxyanisole by weight of the composition, more preferably from 0.06 to 0.4 wt %, still more preferably from 0.08 to 0.2 wt %, and most preferably about 0.1 wt %. Preferably, the butylated hydroxyanisole is predominantly in at least one of the discontinuous oil phase(s). By predominantly in at least one of the discontinuous oil phase(s) it is meant that at least 60 wt % of the butylated hydroxyanisole is in at least one of the discontinuous oil phase(s), preferably at least 70 wt %, and most preferably at least 80 wt %. Preferably, at most 99 wt % of the butylated hydroxyanisole is in at least one of the discontinuous oil phase(s).

Preferably, the polyaphron dispersion further comprises a discontinuous phase comprising a non-solvent oil. By "non-solvent oil" it is meant an oil in which the calcipotriol and/or betamethasone have low solubility (less than 0.0011 wt % for calcipotriol and less than 0.0142 wt % for betamethasone) at 20° C. The inclusion of a further discontinuous phase comprising a non-solvent oil has been found to improve occlusivity and thereby enhance permeation of the active. Moreover, because the further discontinuous phase limits the amount of continuous aqueous phase present in the formulation, it limits the partitioning of the actives to the continuous aqueous phase.

Preferably, the non-solvent oil is present in an amount of at least 5 wt % by weight of the composition, more preferably from 10 to 40 wt %, still more preferably from 20 to 35 wt % by weight of the composition, and most preferably from 25 to 30 wt %. The non-solvent oil is preferably mineral oil and/or silicone oil, more preferably mineral oil.

Preferably, the discontinuous oil phase(s) comprises a first discontinuous phase, a second discontinuous phase and, optionally, a third discontinuous phase comprising mineral oil,
wherein the calcipotriol is predominantly in the first discontinuous phase,
wherein the betamethasone dipropionate is predominantly in the second discontinuous phase, and
wherein the alpha-tocopherol and the butylated hydroxyanisole are predominantly in the first discontinuous phase, or predominantly in the first and second discontinuous phases collectively.

The word "predominantly" takes the same meaning as defined above. It is to be understood that the first discontinuous phase is not dispersed in the second discontinuous phase, or vice versa. In other words, the composition does not contain a complex internal phase, for example as disclosed in WO 2005/082515.

Preferably, the first discontinuous phase and the second discontinuous phase each comprise a pharmaceutically acceptable oil. The first discontinuous phase and the second discontinuous phase may each comprise the same pharmaceutically acceptable oil. Alternatively, the first discontinuous phase and the second discontinuous phase may each comprise different pharmaceutically acceptable oils.

Preferably, the pharmaceutically acceptable oil is a blend of medium chain triglycerides (MCT) and isopropyl myristate (IPM). Preferably, the medium chain triglycerides are present in a total amount of from 2 to 12 wt % by weight of the composition, more preferably from 4 to 10 wt %, and most preferably from 5 to 8 wt %. Preferably, the isopropyl myristate is present in a total amount of from 30 to 50 wt %, more preferably from 35 to 45 wt % and most preferably from 37 to 43 wt %. Preferably, the isopropyl myristate and medium chain triglycerides are present in a weight ratio of from 3:1 to 12:1, more preferably from 4:1 to 8:1. The present inventors have found that blending a small amount of MCT into the API-containing oil phases gives rise to improved dermal diffusion of the actives compared to when IPM is used alone. This is surprising because IPM is a known permeation enhancer and IPM alone would be expected to give better diffusion of the actives than a combination of MCT and IPM. It has been found that the improved active diffusion is only obtained when the MCT and IPM are present in the above (relative) amounts; including too much MCT has been found to have a negative impact on dermal diffusion of the actives. By "medium chain triglycerides" it is meant triglycerides whose constituent fatty acids have an aliphatic tail of from 6 to 12 carbon atoms. Preferably, the medium chain triglycerides are caprylic capric triglycerides.

The alpha-tocopherol and the butylated hydroxyanisole are preferably predominantly in the first discontinuous phase and the second discontinuous phase. Preferably, the alpha-tocopherol is present in the first discontinuous phase and the second discontinuous phase in a weight ratio of from 1:3 to 3:1, more preferably from 1:2 to 2:1, and most preferably about 1:1. Preferably, the butylated hydroxyanisole is present in the first discontinuous phase and the second discontinuous phase in a weight ratio of from 1:3 to 3:1, more preferably from 1:2 to 2:1, and most preferably about 1:1.

Preferably, the first discontinuous phase is present in an amount of from 15 to 30 wt % by weight of the composition, more preferably from 20 to 25 wt %.

Preferably, the second discontinuous phase is present in an amount of from 15 to 30 wt % by weight of the composition, more preferably from 20 to 25 wt %.

Preferably, the third discontinuous phase, where present, is present in an amount of from 5 to 40 wt % by weight of the composition, more preferably from 20 to 35 wt %, and most preferably from 25 to 30 wt %.

Preferably, the first discontinuous phase and the second discontinuous phase are present in a weight ratio of from 1:3 to 3:1, more preferably from 1:2 to 2:1, and most preferably about 1:1.

Preferably, the composition of the present invention comprises a surfactant. The surfactant may be incorporated into one or more of the discontinuous oil phases and/or the continuous aqueous phase. Suitable surfactants include an alkyl polyglycol ether, an alkyl polyglycol ester, an ethoxylated alcohol, a polyoxyethylene sorbitan fatty acid ester, a polyoxyethylene fatty acid ester, an ionic or non-ionic surfactant, a hydrogenated castor oil/polyoxyethylene glycol adduct containing from 25 to 60 ethoxy groups, a castor oil/polyoxyethylene glycol adduct containing from 25 to 45 ethoxy groups, a sorbitan fatty acid ester (for example Span 20 or Span 80), a block copolymer of ethylene oxide and propylene oxide (for example Poloxamer 407 or Poloxamer 188), or a mixture thereof.

Preferably, the composition comprises two or more surfactants, for example a first surfactant incorporated into the one or more discontinuous oil phases, and a second, different surfactant incorporated into the continuous aqueous phase. The first and second surfactants are preferably selected from the list above. The first surfactant readily dissolves or disperses in the oil(s) of the discontinuous phase(s) and is preferably selected from the group consisting of Laureth-4 (polyoxyethylene (4) monododecyl ether), polysorbate 80, Span 80, and mixtures of two or more thereof. The second surfactant readily dissolves or disperses in the continuous aqueous phase and is preferably selected from the group consisting of Polysorbate 20, Poloxamer 407, Poloxamer 188, PEG-40 hydrogenated castor oil, and mixtures of two or more thereof. Most preferably, the first surfactant is Laureth-4 (polyoxyethylene (4) monododecyl ether), and the second surfactant is Poloxamer 407.

Preferably, the composition disclosed herein has a total surfactant content of less than 5 wt % by weight of the composition, more preferably less than 3 wt %, still more preferably less than 2 wt %. Preferably, the total surfactant content is at least 0.5 wt %.

Preferably, the composition of the present invention is dispersible in water. Preferably the composition of the present invention is dilutable in water. This increases the flexibility of use of the invention, for example in improving the application of the composition to the scalp through hair by leaving the hair wet, or from rinsing the preparation from any topical surface should the desire or need arise, or by the easy removal by rinsing of product from accidental contamination of clothing. These advantages improve the in-use experience of users and improve patient compliance.

Preferably, the composition of the present invention further comprises a gelling agent and/or a rheology modifying agent, such as a viscosity modifier. The gelling agent may, for example, be selected from alginate gums or their salts, guar gum, locust bean gum, xanthan gum, gum acacia, gelatin, hydroxymethylcellulose, hydroxyethylcellulose, hydroxypropylcellulose, carboxymethylcellulose or its salts, bentonites, magnesium aluminium silicates, "Carbomers" (salts of cross-linked polymers of acrylic acid), or glyceryl polymethacrylates or their dispersions in glycols. It will be understood that other suitable gelling agents may be used. Additionally, it has been found that some of the gelling agents (for example, carbomers) may also function as a chemical buffering agents thus preventing unwanted variation in the pH of the composition during storage and use. Where a viscosity modifier is used, this is preferably a polymeric cellulosic thickener. The inclusion of a gelling agent and/or rheology modifying agent provides additional stability against creaming and ensures that the active concentration is uniform throughout the composition. The use of these components is described in WO97/32559. The choice of gelling/thickening agents also allows for control of formulation viscosity from a thin lotion that is readily pourable to a thick cream with a significant resistance to flow.

Preferably, the composition of the present invention comprises from 0.05 to 5.0% by weight of a gelling agent, preferably from 0.1 to 2.0% by weight and more preferably from 0.2 to 1.0% by weight of the composition. In one embodiment of the present invention the composition has the consistency of a gel.

The compositions of the present invention may also contain other additives such as preservatives (for instance to prevent microbiological spoilage), buffering agents (for the control of pH and to avoid instability and damage to the skin's acid mantle) and antioxidants. Where a preservative is used, it is preferably present in an amount of from 0.5 to 1 wt %, more preferably from 0.6 to 0.8 wt %, by weight of the composition. The preservative is preferably selected from the group consisting of benzyl alcohol, phenoxyethanol, methyl paraben, propyl paraben and mixtures of two or more thereof. Most preferably, the preservative is phenoxyethanol. These additives may be included in the continuous or the discontinuous phase(s) of the polyaphron dispersion. It will be understood that the inclusion of these additives will be at the levels and with the type of materials which are found to be effective and useful. Care needs to be taken in the choice and amount of these additives to prevent compromise to the other performance advantages of the present invention.

Especially preferred embodiments of the first aspect of the present invention will now be described.

In an especially preferred embodiment, the composition of the present invention comprises a polyaphron dispersion, the polyaphron dispersion comprising a continuous aqueous phase and at least one discontinuous oil phase,
 wherein the polyaphron dispersion comprises calcipotriol, betamethasone dipropionate, alpha-tocopherol and butylated hydroxyanisole, and
 wherein the composition has a pH of 7.75±0.5,
 wherein the composition comprises, by weight of the composition:
 from 0.002 to 0.008 wt % calcipotriol;
 from 0.04 to 0.08 wt % betamethasone;
 from 0.0015 to 0.003 wt % alpha-tocopherol; and
 from 0.08 to 0.2 wt % butylated hydroxyanisole;
 wherein at least 60 wt % of the calcipotriol is in at least one of said discontinuous oil phase(s),
 wherein at least 60 wt % of the betamethasone dipropionate is in at least one of said discontinuous oil phase(s),
 wherein at least 60 wt % of the alpha-tocopherol is in at least one of said discontinuous oil phase(s),
 wherein at least 60 wt % of the butylated hydroxyanisole is in at least one of said discontinuous oil phase(s).
 wherein the polyaphron dispersion further comprises a discontinuous phase comprising mineral oil, and
 wherein the composition is in the form of a lotion or cream.

In an especially preferred embodiment, the composition of the present invention comprises a polyaphron dispersion, the polyaphron dispersion comprising a continuous aqueous phase and at least one discontinuous oil phase,
  wherein the polyaphron dispersion comprises calcipotriol, betamethasone dipropionate, alpha-tocopherol and butylated hydroxyanisole, and
  wherein the composition has a pH of 7.75±0.5,
  wherein the composition comprises, by weight of the composition:
  from 0.002 to 0.008 wt % calcipotriol;
  from 0.04 to 0.08 wt % betamethasone;
  from 0.0015 to 0.003 wt % alpha-tocopherol; and
  from 0.08 to 0.2 wt % butylated hydroxyanisole;
  wherein at least 60 wt % of the calcipotriol is in at least one of said discontinuous oil phase(s),
  wherein at least 60 wt % of the betamethasone dipropionate is in at least one of said discontinuous oil phase(s),
  wherein at least 60 wt % of the alpha-tocopherol is in at least one of said discontinuous oil phase(s),
  wherein at least 60 wt % of the butylated hydroxyanisole is in at least one of said discontinuous oil phase(s),
  wherein the at least one discontinuous oil phase is present in a total amount of from 10 to 90 wt % by weight of the composition, and
  wherein the continuous aqueous phase is present in an amount of from 10 to 90 wt % by weight of the composition.

In a further especially preferred embodiment, the composition of the present invention comprises a polyaphron dispersion, the polyaphron dispersion comprising a continuous aqueous phase and at least one discontinuous oil phase,
  wherein the polyaphron dispersion comprises calcipotriol, betamethasone dipropionate, alpha-tocopherol and butylated hydroxyanisole, and
  wherein the composition has a pH of 7.75±0.5,
  wherein the composition comprises, by weight of the composition:
  from 0.002 to 0.008 wt % calcipotriol;
  from 0.04 to 0.08 wt % betamethasone;
  from 0.0015 to 0.003 wt % alpha-tocopherol; and
  from 0.08 to 0.2 wt % butylated hydroxyanisole;
  wherein at least 60 wt % of the calcipotriol is in at least one of said discontinuous oil phase(s),
  wherein at least 60 wt % of the betamethasone dipropionate is in at least one of said discontinuous oil phase(s),
  wherein at least 60 wt % of the alpha-tocopherol is in at least one of said discontinuous oil phase(s),
  wherein at least 60 wt % of the butylated hydroxyanisole is in at least one of said discontinuous oil phase(s),
  wherein at least one of said discontinuous phase(s) comprises caprilic capric triglycerides and isopropyl myristate, wherein the caprilic capric triglycerides are present in a total amount of from 4 to 10 wt % by weight of the composition, wherein the isopropyl myristate is present in a total amount of from 35 to 45 wt % by weight of the composition, and wherein the isopropyl myristate and caprilic capric triglycerides are present in a weight ratio of from 4:1 to 8:1,
  wherein the polyaphron dispersion further comprises a discontinuous phase comprising mineral oil, and
  wherein the composition is in the form of a lotion or cream.

In a further especially preferred embodiment, the composition of the present invention comprises a polyaphron dispersion, the polyaphron dispersion comprising a continuous aqueous phase and at least one discontinuous oil phase,
  wherein the polyaphron dispersion comprises calcipotriol, betamethasone dipropionate, alpha-tocopherol and butylated hydroxyanisole, and
  wherein the composition has a pH of 7.75±0.5,
  wherein said discontinuous oil phase(s) comprise, by weight of the composition:
  from 15 to 30 wt % of a first discontinuous phase comprising a blend of caprilic capric triglycerides and isopropyl myristate, wherein the isopropyl myristate and caprilic capric triglycerides are present in a weight ratio of from 4:1 to 8:1,
  from 15 to 30 wt % of a second discontinuous phase comprising a blend of caprilic capric triglycerides and isopropyl myristate, wherein the isopropyl myristate and caprilic capric triglycerides are present in a weight ratio of from 4:1 to 8:1,
  from 20 to 30 wt % of a third discontinuous phase comprising mineral oil,
  wherein at least 60 wt % of the calcipotriol is in the first discontinuous phase,
  wherein at least 60 wt % of the betamethasone dipropionate is in the second discontinuous phase,
  wherein at least 60 wt % of the alpha-tocopherol and the butylated hydroxyanisole are in the first discontinuous phase and the second discontinuous phase,
  wherein the continuous aqueous phase comprises from 4 to 10 wt % isopropanol by weight of the composition,
  wherein the alpha-tocopherol is present in the first discontinuous phase and the second discontinuous phase in a weight ratio of from 1:2 to 2:1,
  wherein the butylated hydroxyanisole is present in the first discontinuous phase and the second discontinuous phase in a weight ratio of from 1:2 to 2:1, and
  wherein the composition is in the form of a lotion or cream.

In a further especially preferred embodiment, the composition of the present invention comprises a polyaphron dispersion, the polyaphron dispersion comprising a continuous aqueous phase and at least one discontinuous oil phase,
  wherein the polyaphron dispersion comprises calcipotriol, betamethasone dipropionate, alpha-tocopherol and butylated hydroxyanisole, and
  wherein the composition has a pH of 7.75±0.5,
  wherein said discontinuous oil phase(s) comprise, by weight of the composition:
  from 15 to 30 wt % of a first discontinuous phase comprising a blend of caprilic capric triglycerides and isopropyl myristate, wherein the isopropyl myristate and caprilic capric triglycerides are present in a weight ratio of from 4:1 to 8:1,
  from 15 to 30 wt % of a second discontinuous phase comprising a blend of caprilic capric triglycerides and isopropyl myristate, wherein the isopropyl myristate and caprilic capric triglycerides are present in a weight ratio of from 4:1 to 8:1,
  from 25 to 35 wt % of a third discontinuous phase comprising mineral oil,
  wherein the composition comprises, by weight of the composition:
  from 0.002 to 0.008 wt % calcipotriol;
  from 0.04 to 0.08 wt % betamethasone;
  from 0.0015 to 0.003 wt % alpha-tocopherol; and
  from 0.08 to 0.2 wt % butylated hydroxyanisole;
  wherein at least 60 wt % of the calcipotriol is in the first discontinuous phase,
  wherein at least 60 wt % of the betamethasone dipropionate is in the second discontinuous phase, wherein at least 60 wt % of the alpha-tocopherol and the butylated hydroxyanisole are in the first discontinuous phase and the second discontinuous phase, wherein the continuous aqueous phase comprises from 4 to 10 wt % isopropanol by weight of the composition, wherein the alpha-tocopherol is present in the first discontinuous phase and the second discontinuous phase in a weight ratio of from 1:2 to 2:1, wherein the butylated hydroxyanisole is present in the first discontinuous phase and the second discontinuous phase in a weight ratio of from 1:2 to 2:1, and wherein the composition is in the form of a lotion or cream.

In a further especially preferred embodiment, the composition of the present invention comprises a polyaphron dispersion, the polyaphron dispersion comprising a continuous aqueous phase and at least one discontinuous oil phase, wherein the polyaphron dispersion comprises calcipotriol, betamethasone dipropionate, alpha-tocopherol and butylated hydroxyanisole, and wherein the composition has a pH of 7.75±0.5, wherein said discontinuous oil phase(s) comprise, by weight of the composition:

from 15 to 30 wt % of a first discontinuous phase comprising a blend of caprilic capric triglycerides and isopropyl myristate, wherein the isopropyl myristate and caprilic capric triglycerides are present in a weight ratio of from 4:1 to 8:1, from 15 to 30 wt % of a second discontinuous phase comprising a blend of caprilic capric triglycerides and isopropyl myristate, wherein the isopropyl myristate and caprilic capric triglycerides are present in a weight ratio of from 4:1 to 8:1, from 20 to 35 wt % of a third discontinuous phase comprising mineral oil, wherein the composition comprises, by weight of the composition:

from 0.002 to 0.008 wt % calcipotriol;
from 0.04 to 0.08 wt % betamethasone;
from 0.0015 to 0.003 wt % alpha-tocopherol; and
from 0.08 to 0.2 wt % butylated hydroxyanisole;

wherein at least 95 wt % of the calcipotriol is in the first discontinuous phase, wherein at least 95 wt % of the betamethasone dipropionate is in the second discontinuous phase, wherein at least 95 wt % of the alpha-tocopherol and the butylated hydroxyanisole are in the first discontinuous phase and the second discontinuous phase, wherein the continuous aqueous phase comprises from 15 to 25 wt % water and from 4 to 10 wt % isopropanol by weight of the composition, wherein the alpha-tocopherol is present in the first discontinuous phase and the second discontinuous phase in a weight ratio of from 1:2 to 2:1, wherein the butylated hydroxyanisole is present in the first discontinuous phase and the second discontinuous phase in a weight ratio of from 1:2 to 2:1, wherein the composition is in the form of a lotion or cream, and wherein the composition is chemically and physically stable for at least 6 months at 25° C.±2° C., as measured at 60% RH±5%.

The foregoing especially preferred embodiments may be freely combined with the preferred embodiments described elsewhere in the specification.

According to a second aspect, there is provided a composition for topical application comprising a polyaphron dispersion, the polyaphron dispersion comprising a continuous aqueous phase and at least one discontinuous oil phase, wherein the polyaphron dispersion comprises calcipotriol, betamethasone dipropionate, alpha-tocopherol and butylated hydroxyanisole, wherein at least one of said discontinuous oil phase(s) comprises medium chain triglycerides and isopropyl myristate, and wherein the isopropyl myristate and medium chain triglycerides are present in a weight ratio of from 3:1 to 12:1.

The composition of the second aspect may be freely combined with the preferred features of the composition of the first aspect.

According to a third aspect, there is provided a composition for topical application comprising a polyaphron dispersion, wherein the polyaphron dispersion comprises:

(i) calcipotriol;
(ii) betamethasone or an ester thereof;
(iii) alpha-tocopherol; and
(iv) butylated hydroxyanisole.

The composition of the third aspect may be freely combined with the preferred features of the compositions of the first and second aspects.

According to a further aspect, there is provided a composition as described herein for use in the treatment of the human or animal body by therapy.

According to a further aspect, there is provided a method of treatment of the human or animal body by therapy, the method comprising administering to a subject in need thereof an effective amount of a composition as described herein.

According to a further aspect, there is provided the use of a composition as described herein for the manufacture of a medicament for the treatment of a human or animal subject by therapy.

According to a further aspect, there is provided a composition as described herein for use in the treatment of psoriasis.

According to a further aspect, there is provided a method of treating psoriasis in a human or animal subject comprising administering to a subject in need thereof an effective amount of a composition as described herein.

According to a further aspect, there is provided the use of a composition as described herein for the manufacture of a medicament for the treatment of psoriasis in a human or animal subject.

The composition as described herein may be applied to the scalp or other skin surface through hair. Preferably in this embodiment the hair is wetted (for example by use of water with or without shampoo, and then towel dried). The product may then be applied to the scalp in a suitable amount and then massaged into the scalp through the hair. The hair may then be left to dry naturally or dried using a hair dryer. Advantageously, the water-dispersible form of the formulation enables an even distribution of the actives on the skin using this process. Alternatively, or additionally, the composition may be massaged into the scalp through dry hair and left for a suitable period (which may be 8 to 12 hours) after which the excess or reminder may be rinsed out with water with or without shampoo.

According to a further aspect, there is provided a package comprising the composition described herein. Preferably, the package is a tube or an airless pump. For example, a tube can be squeezed for topical application of the composition.

According to a further aspect, there is provided a method of manufacturing a composition for topical application, the method comprising:
(a) preparing a first polyaphron dispersion comprising calcipotriol, alpha-tocopherol and butylated hydroxyanisole;
(b) preparing a second polyaphron dispersion comprising betamethasone dipropionate and preferably further comprising alpha-tocopherol and butylated hydroxyanisole; and
mixing together the first and second polyaphron dispersions to form the composition.

Preferably, the composition produced by the method is the composition as defined above.

It will be appreciated that while the calcipotriol and the betamethasone dipropionate are provided in separate polyaphron dispersions during the method of manufacture, upon mixing these form a single polyaphron dispersion comprising two discontinuous phases: one discontinuous phase comprising calcipotriol, and another discontinuous phase comprising betamethasone dipropionate. It is therefore to be understood that upon mixing of the first and second polyaphron dispersions, the oil phases will remain distinct but that the continuous phases will merge, i.e. there will be one continuous phase within which individual oil droplets derived from the first and second polyaphron dispersions will be dispersed.

Preferably, the method further comprises preparing a third polyaphron dispersion comprising mineral oil, and mixing the third polyaphron dispersion with the first and second polyaphron dispersions to form the composition. Again, while this embodiment involves the use of a third polyaphron dispersion, upon mixing with first and second polyaphron dispersions a single polyaphron dispersion comprising three discontinuous phases is formed: one discontinuous phase comprising calcipotriol, a second discontinuous phase comprising betamethasone dipropionate and a third discontinuous phase comprising mineral oil. It is therefore to be understood that upon mixing of the first, second and third polyaphron dispersions, the oil phases will remain distinct but that the continuous phases will merge, i.e. there will be one continuous phase within which individual oil droplets derived from the first, second and third polyaphron dispersions will be dispersed.

Preferably, the method further comprises packaging the composition.

According to a further aspect, there is provided a composition obtainable by the method as defined herein.

According to a further aspect, there is provided the use of a combination of alpha-tocopherol and butylated hydroxyanisole in a composition for topical application to stabilise:
(i) calcipotriol; and/or
(ii) betamethasone dipropionate.

The present invention will now be described in relation to the following non-limiting figures.

Figure 1:
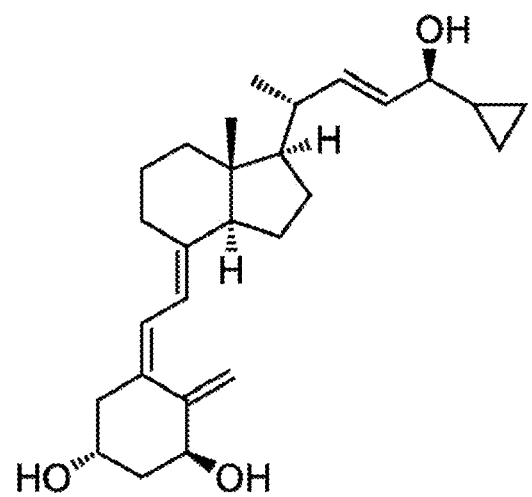
FIG. 1 depicts the chemical structure of calcipotriol.
Figure 2:
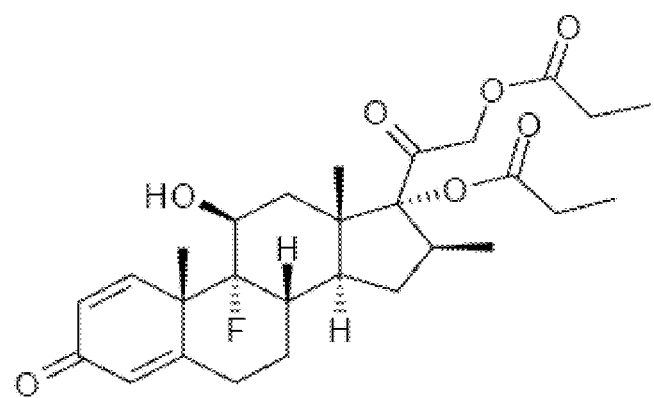
FIG. 2 depicts the chemical structure of betamethasone dipropionate.
Figure 3:
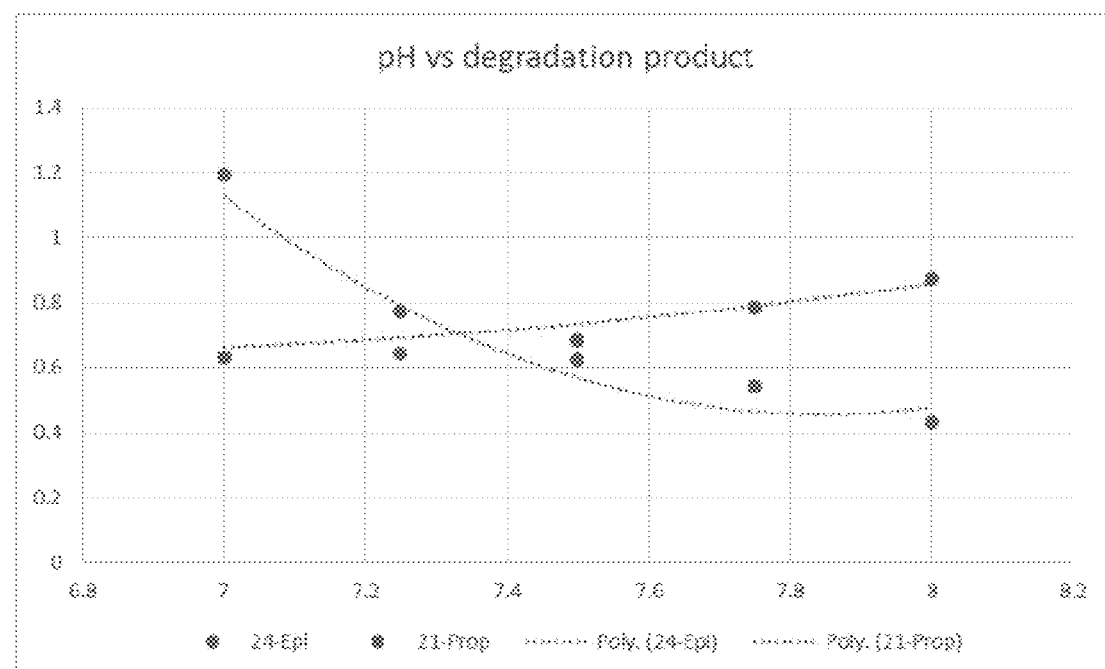

FIG. 3 shows the variation in the amounts of the principal degradation products of calcipotriol (24-epi calcipotriol, lighter filled circles) and betamethasone dipropionate (betamethasone 21-propionate, darker filled circles) with pH in polyaphron compositions containing the two actives, as measured after storage for 9 months at 5° C. The y-axis represents the level of a degradation product, as determined from an HPLC chromatogram and including related peaks, as a percentage of the total active pharmaceutical ingredient from which it is derived.

Figure 4:
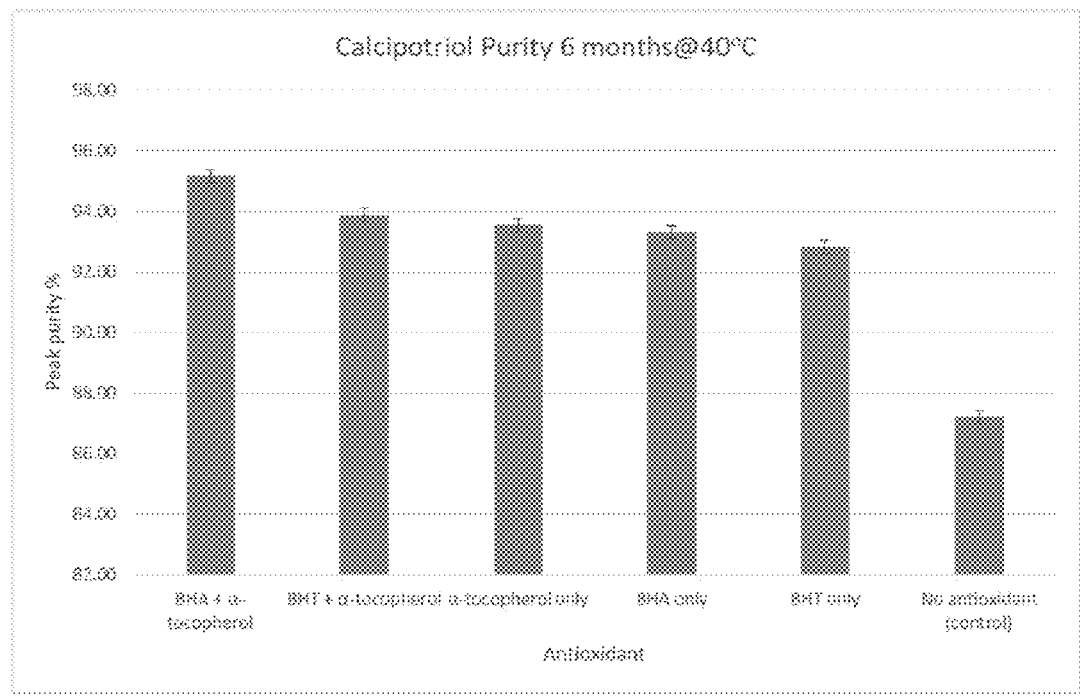

FIG. 4 shows the chemical stability of calcipotriol in polyaphron compositions as determined by the purity method described herein for different combinations of antioxidants. The error bars indicate standard deviation.

Figure 5:
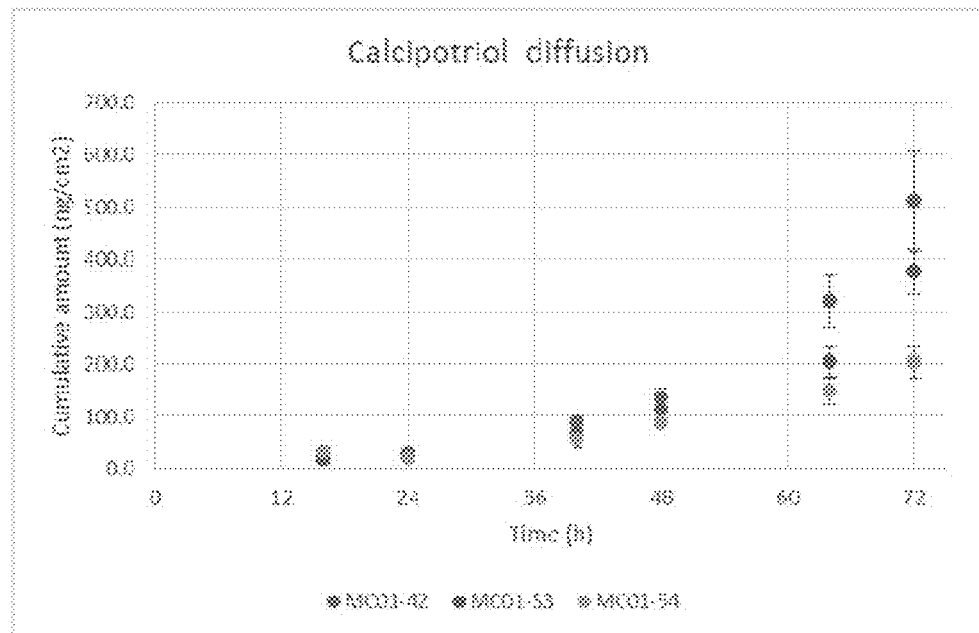

FIG. 5 shows the cumulative amount of calcipotriol diffused through human skin over 72 hours from the three formulations tested in Example 9. The x-axis represents time in hours and the y-axis represents the mean cumulative amount of calcipotriol diffused through the skin in $ng/cm^2$. The darkest filled circles represent MC01-53, the intermediate filled circles represent MC01-42, and the lightest filled circles represent MC01-54. The error bars indicate standard error of the mean.

Figure 6:
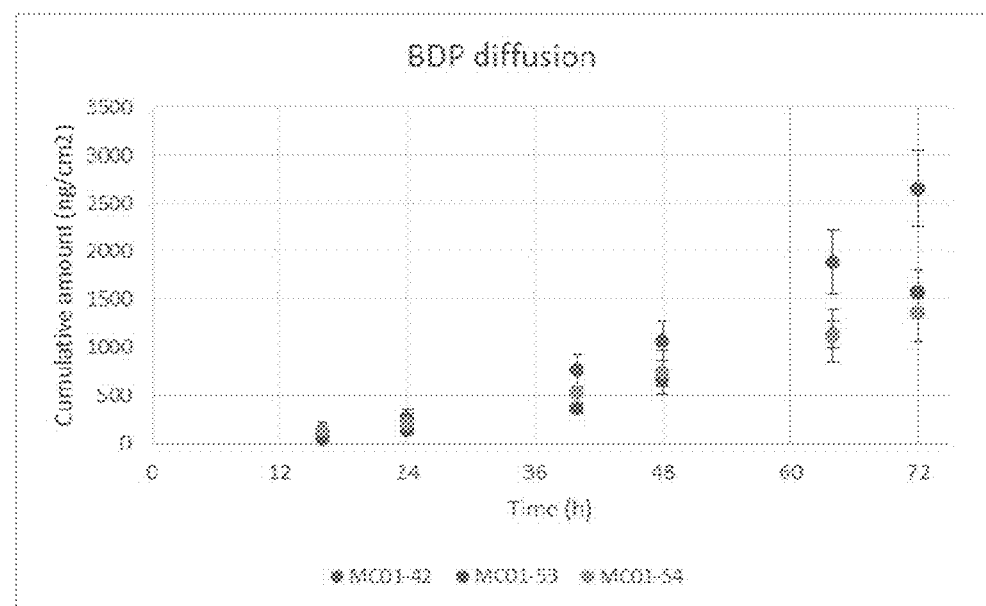

FIG. 6 shows the cumulative amount of betamethasone dipropionate diffused through human skin over 72 hours from the three formulations tested in Example 9. The x-axis represents time in hours and the y-axis represents the mean cumulative amount of betamethasone dipropionate diffused through the skin in $ng/cm^2$. The darkest filled circles represent MC01-53, the intermediate filled circles represent MC01-42, and the lightest filled circles represent MC01-54. The error bars indicate standard deviation.

Figure 7:
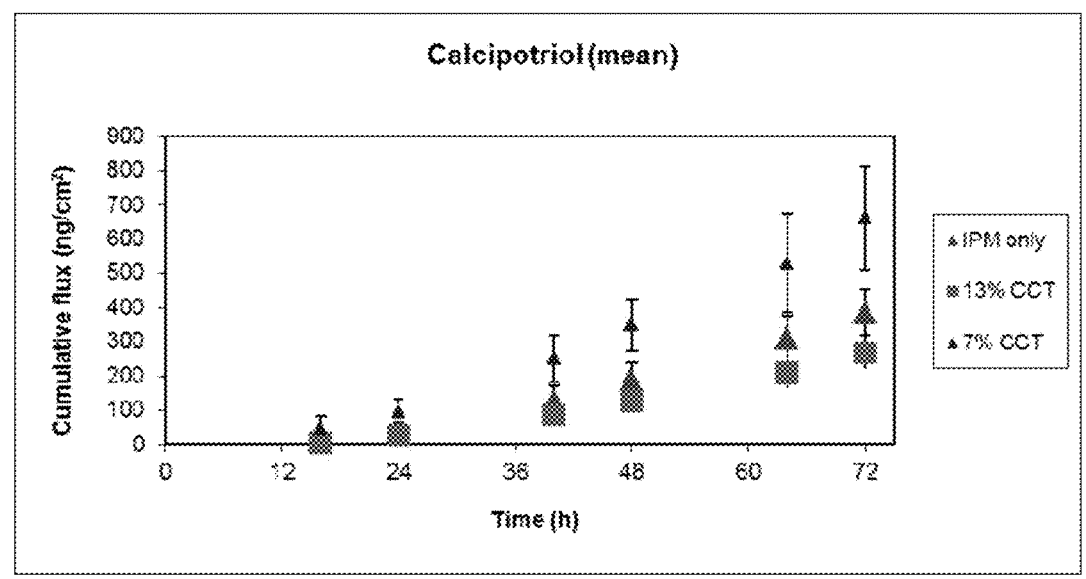

FIG. 7 shows the cumulative amount of calcipotriol diffused through human skin over 72 hours from the polyaphron dispersion-containing formulations tested in Example 10. The x-axis represents time in hours and the y-axis represents the mean cumulative amount of calcipotriol diffused through the skin in $ng/cm^2$. The small dark triangles represent 7% CCT, the larger lighter triangles represent IPM only, and the squares represent 13% CCT. The error bars indicate standard deviation.

Figure 8:
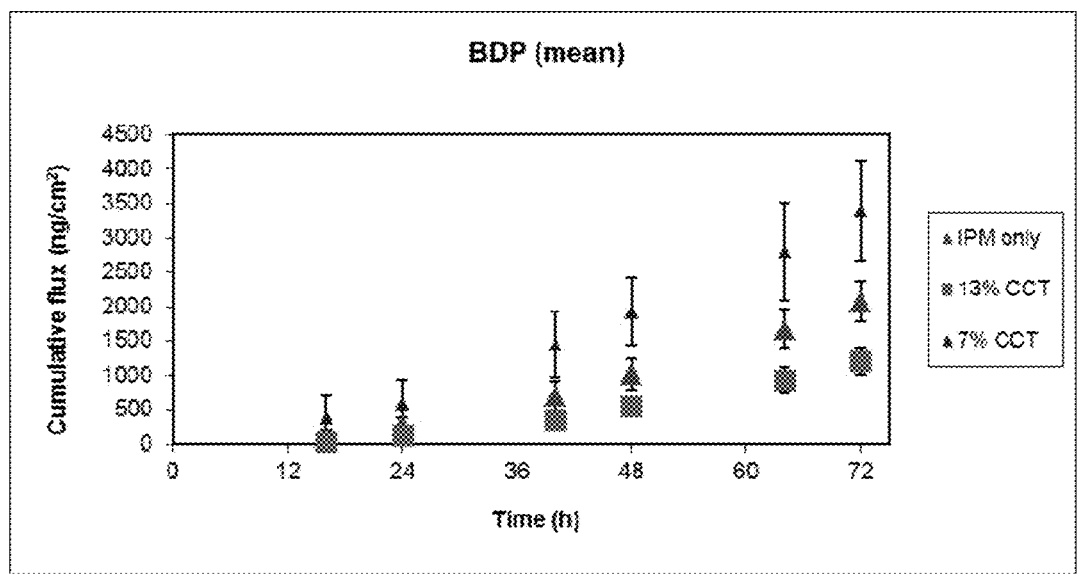

FIG. 8 shows the cumulative amount of betamethasone dipropionate diffused through human skin over 72 hours from the polyaphron dispersion-containing formulations tested in Example 10. The x-axis represents time in hours and the y-axis represents the mean cumulative amount of betamethasone dipropionate diffused through the skin in $ng/cm^2$. The small dark triangles represent 7% CCT, the larger lighter triangles represent IPM only, and the squares represent 13% CCT. The error bars indicate standard deviation.

Figure 9:
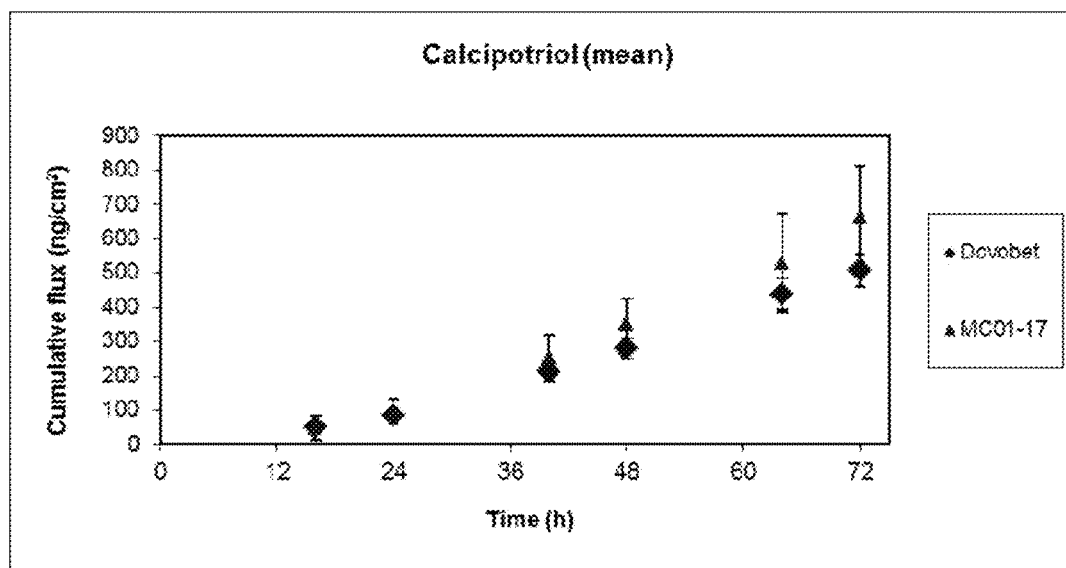

FIG. 9 shows the cumulative amount of calcipotriol diffused through human skin over 72 hours from a formulation in accordance with the invention (MC01-17, triangles) compared with commercially available Dovobet® ointment (diamonds). The x-axis represents time in hours and the y-axis represents the mean cumulative amount of calcipotriol diffused through the skin in $ng/cm^2$. The error bars indicate standard deviation.

Figure 10:
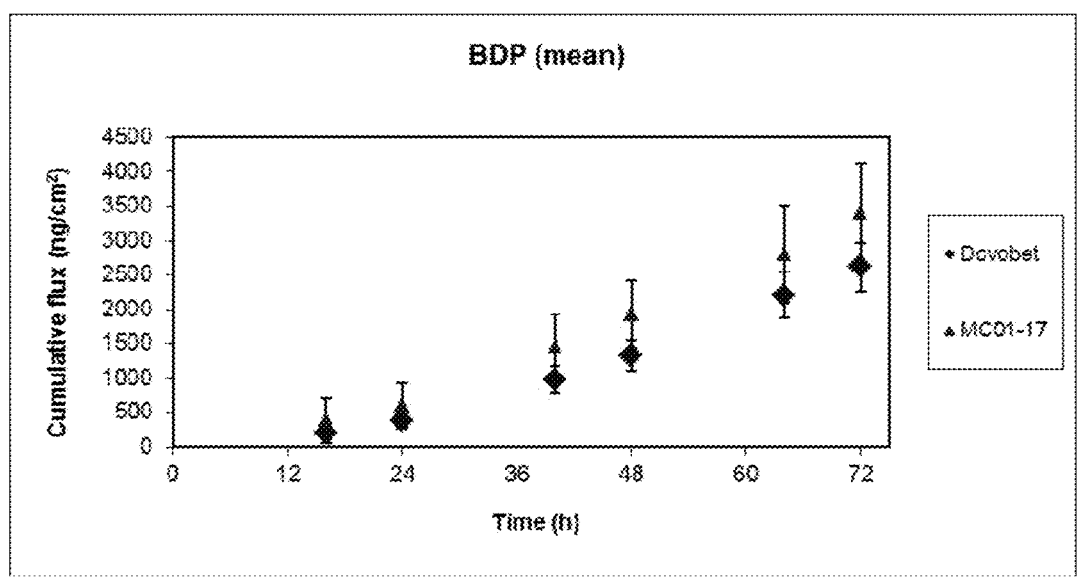

FIG. 10 shows the cumulative amount of betamethasone dipropionate diffused through human skin over 72 hours from a formulation in accordance with the invention (MC01-17, triangles) compared with commercially available Dovobet® ointment (diamonds). The x-axis represents time in hours and the y-axis represents the mean cumulative amount of betamethasone dipropionate diffused through the skin in $ng/cm^2$. The error bars indicate standard deviation.

The present invention will now be described in relation to the following non-limiting examples.

EXAMPLE 1

A composition in accordance with the present invention was prepared by combining the following components.

| Component | | Ingredient | % wt/wt | % wt/wt |
|---|---|---|---|---|
| A (Calcipotriol containing polyaphron) | Oil phase | Calcipotriol base | 0.005 | 28.12466 |
| | | Isopropyl myristate | 16.668 | |
| | | Capric/caprylic triglycerides | 5.556 | |
| | | Laureth-4 | 0.25 | |
| | | Butylated hydroxyanisole | 0.05 | |
| | | α-tocopherol | 0.0006625 | |
| | Aqueous phase | Poloxamer 407 | 0.28 | |
| | | Isopropyl alcohol | 1.00 | |
| | | Water | 4.315 | |
| B (Betamethasone dipropionate containing polyaphron) | Oil phase | Betamethasone dipropionate | 0.0644 | 28.12506 |
| | | Isopropyl myristate | 16.625 | |
| | | Capric/caprylic triglycerides | 5.54 | |
| | | Laureth-4 | 0.25 | |
| | | Butylated hydroxyanisole | 0.05 | |
| | | α-tocopherol | 0.0006625 | |
| | | Poloxamer 407 | 0.28 | |
| | Aqueous phase | Isopropyl alcohol | 1.00 | |
| | | Water | 4.315 | |
| C (Mineral oil polyaphron) | Oil phase | Mineral oil | 26.70 | 33.75 |
| | | Laureth-4 | 0.30 | |
| | Aqueous phase | Cremophor RH40 | 0.337 | |
| | | Isopropyl alcohol | 2.025 | |
| | | Water | 4.388 | |
| D (Buffer phase) | | Disodium phosphate heptahydrate | 0.0291 | 1.00 |
| | | Mono sodium phosphate monohydrate | 0.0044 | |
| | | Water | 0.9665 | |
| E (Gel phase) | | Carbomer (Ultrez 10) | 0.20 | 7.00 |
| | | Water | 6.80 | |
| F | | Water | 0.30 | 0.30 |
| G (pH and adjust) | | Triethanolamine (50% wt/wt aqueous solution) | q.s. | q.s. |
| | | Water | q.s. | |
| | | | | 100.00 |

The polyaphron sub-component A was made by firstly mixing the components of the oil phase together at 40° C. until fully dissolved and then allowed to cool. The aqueous phase components were also mixed with suitable stirring until fully dissolved. The oil phase was then slowly added to the aqueous phase with continuous moderate stirring. After the full oil addition the dispersion was then mixed for a further 30 minutes. The polyaphron sub-components B & C were made using the same method. The buffer phase D was mixed in a separate vessel. In another suitable vessel the gel phase (E) was made by adding the carbomer to the water with vigorous mixing until fully dispersed and hydrated.

The final formulation was then made by mixing the polyaphron sub components (A, B & C) together in a vessel using moderate mixing. The gel phase (E) was then added to this and mixed followed by the addition of the Buffer phase (D) and the additional isopropanol (F). The formulation was then adjusted to pH7.75 using the required amount of triethanolamine 50% wt aqueous solution before being adjusted to 100% wt by the addition of water. The formula was made on a 1 kg scale.

EXAMPLE 2

A further composition in accordance with the present invention was prepared by combining the following components:

| Component | | Ingredient | % wt/wt | % wt/wt |
|---|---|---|---|---|
| A (Calcipotriol containing polyaphron) | Oil phase | Calcipotriol base | 0.005 | 28.12466 |
| | | Isopropyl myristate | 20.204 | |
| | | Capric/caprylic triglycerides | 2.02 | |
| | | Laureth-4 | 0.25 | |
| | | Butylated hydroxyanisole | 0.05 | |
| | | α-tocopherol | 0.0006625 | |
| | Aqueous phase | Poloxamer 407 | 0.28 | |
| | | Isopropyl alcohol | 2.00 | |
| | | Water | 3.315 | |

-continued

| Component | | Ingredient | % wt/wt | % wt/wt |
|---|---|---|---|---|
| B (Betamethasone dipropionate containing polyaphron) | Oil phase | Betamethasone dipropionate | 0.0644 | 28.12506 |
| | | Isopropyl myristate | 20.15 | |
| | | Capric/caprylic triglycerides | 2.015 | |
| | | Laureth-4 | 0.25 | |
| | | Butylated hydroxyanisole | 0.05 | |
| | | α-tocopherol | 0.0006625 | |
| | Aqueous phase | Poloxamer 407 | 0.28 | |
| | | Isopropyl alcohol | 2.00 | |
| | | Water | 3.315 | |
| C (Mineral oil polyaphron) | Oil phase | Mineral oil | 26.70 | 33.75 |
| | | Laureth-4 | 0.30 | |
| | Aqueous phase | Cremophor RH40 | 0.337 | |
| | | Isopropyl alcohol | 2.50 | |
| | | Water | 3.913 | |
| D (Buffer phase) | | Disodium phosphate heptahydrate | 0.0291 | 1.00 |
| | | Mono sodium phosphate monohydrate | 0.0044 | |
| | | Water | 0.9665 | |
| E (Gel phase) | | Carbomer (Ultrez 10) | 0.20 | 7.00 |
| | | Water | 6.80 | |
| F | | Isopropyl alcohol | 0.30 | 0.30 |
| G (pH and adjust) | | Triethanolamine (50% wt/wt aqueous solution) | q.s. | q.s. |
| | | Water | q.s. | |
| | | | | 100.00 |

The components were combined analogously to Example 1.

EXAMPLE 3

A composition in accordance with the present invention was prepared by combining the following components:

| Component | | Ingredient | % wt/wt | % wt/wt |
|---|---|---|---|---|
| A (Calcipotriol containing polyaphron) | Oil phase | Calcipotriol base | 0.005 | 28.12466 |
| | | Isopropyl myristate | 20.514 | |
| | | Capric/caprylic triglycerides | 1.71 | |
| | | Laureth-4 | 0.25 | |
| | | Butylated hydroxyanisole | 0.05 | |
| | | α-tocopherol | 0.0006625 | |
| | Aqueous phase | Poloxamer 407 | 0.28 | |
| | | Isopropyl alcohol | 2.00 | |
| | | Water | 3.315 | |
| B (Betamethasone dipropionate containing polyaphron) | Oil phase | Betamethasone dipropionate | 0.0644 | 28.12506 |
| | | Isopropyl myristate | 20.46 | |
| | | Capric/caprylic triglycerides | 1.705 | |
| | | Laureth-4 | 0.25 | |
| | | Butylated hydroxyanisole | 0.05 | |
| | | α-tocopherol | 0.0006625 | |
| | Aqueous phase | Poloxamer 407 | 0.28 | |
| | | Isopropyl alcohol | 2.00 | |
| | | Water | 3.315 | |
| C (Mineral oil polyaphron) | Oil phase | Mineral oil | 13.35 | 16.875 |
| | | Laureth-4 | 0.15 | |
| | Aqueous phase | Cremophor RH40 | 0.1685 | |
| | | Isopropyl alcohol | 1.25 | |
| | | Water | 1.9565 | |
| D (Buffer phase) | | Disodium phosphate heptahydrate | 0.0291 | 1.00 |
| | | Mono sodium phosphate monohydrate | 0.0044 | |
| | | Water | 0.9665 | |
| E (Gel phase) | | Carbomer (Ultrez 10) | 0.20 | 7.00 |
| | | Water | 6.80 | |
| F | | Water | 17.00 | 18.25 |
| | | Isopropyl alcohol | 1.25 | |

| Component | | Ingredient | % wt/wt | % wt/wt |
|---|---|---|---|---|
| G (pH and adjust) | | Triethanolamine (50% wt/wt aqueous solution) | q.s. | q.s. |
| | | Water | q.s. | |
| | | | | 100.00 |

The components were combined analogously to Example 1.

EXAMPLE 4

A composition in accordance with the present invention was prepared by combining the following components:

| Component | | Ingredient | % wt/wt | % wt/wt |
|---|---|---|---|---|
| A (Calcipotriol containing polyaphron) | Oil phase | Calcipotriol base | 0.005 | 28.12466 |
| | | Isopropyl myristate | 18.849 | |
| | | Capric/caprylic triglycerides | 3.375 | |
| | | Laureth-4 | 0.25 | |
| | | Butylated hydroxyanisole | 0.05 | |
| | | α-tocopherol | 0.0006625 | |
| | Aqueous phase | Poloxamer 407 | 0.28 | |
| | | Isopropyl alcohol | 1.70 | |
| | | Water | 3.615 | |
| B (Betamethasone dipropionate containing polyaphron) | Oil phase | Betamethasone dipropionate | 0.0644 | 28.12506 |
| | | Isopropyl myristate | 18.79 | |
| | | Capric/caprylic triglycerides | 3.375 | |
| | | Laureth-4 | 0.25 | |
| | | Butylated hydroxyanisole | 0.05 | |
| | | α-tocopherol | 0.0006625 | |
| | Aqueous phase | Poloxamer 407 | 0.28 | |
| | | Isopropyl alcohol | 1.70 | |
| | | Water | 3.615 | |
| C (Mineral oil polyaphron) | Oil phase | Dimethicone (Dow corning Q7-9120 Silicone Fluid, 350 cst) | 26.70 | 33.75 |
| | | Laureth-4 | 0.30 | |
| | Aqueous phase | Cremophor RH40 | 0.337 | |
| | | Isopropyl alcohol | 2.025 | |
| | | Water | 4.388 | |
| D (Buffer phase) | | Disodium phosphate heptahydrate | 0.0291 | 1.00 |
| | | Mono sodium phosphate monohydrate | 0.0044 | |
| | | Water | 0.9665 | |
| E (Gel phase) | | Carbomer (Ultrez 10) | 0.20 | 7.00 |
| | | Water | 6.8 | |
| F | | Isopropyl alcohol | 0.30 | 0.30 |
| G (pH and adjust) | | Triethanolamine (50% wt/wt aqueous solution) | q.s. | q.s. |
| | | Water | q.s. | |
| | | | | 100.00 |

The components were combined analogously to Example 1.

EXAMPLE 5

A composition in accordance with the present invention (MC01-42) was prepared by combining the following components:

| Component | | Ingredient | % wt/wt | % wt/wt |
|---|---|---|---|---|
| A (Calcipotriol containing polyaphron) | Oil phase | Calcipotriol base | 0.005 | 28.12466 |
| | | Isopropyl myristate | 18.849 | |
| | | Capric/caprylic triglycerides | 3.375 | |
| | | Laureth-4 | 0.25 | |

| Component | | Ingredient | % wt/wt | % wt/wt |
|---|---|---|---|---|
| | | Butylated hydroxyanisole | 0.05 | |
| | | α-tocopherol | 0.0006625 | |
| | Aqueous phase | Poloxamer 407 | 0.28 | |
| | | Isopropyl alcohol | 1.70 | |
| | | Water | 3.615 | |
| B (Betamethasone dipropionate containing polyaphron) | Oil phase | Betamethasone dipropionate | 0.0644 | 28.12506 |
| | | Isopropyl myristate | 18.79 | |
| | | Capric/caprylic triglycerides | 3.375 | |
| | | Laureth-4 | 0.25 | |
| | | Butylated hydroxyanisole | 0.05 | |
| | | α-tocopherol | 0.0006625 | |
| | Aqueous phase | Poloxamer 407 | 0.28 | |
| | | Isopropyl alcohol | 1.70 | |
| | | Water | 3.615 | |
| C (Mineral oil polyaphron) | Oil phase | Mineral oil | 26.70 | 33.75 |
| | | Laureth-4 | 0.30 | |
| | Aqueous phase | Cremophor RH40 | 0.337 | |
| | | Isopropyl alcohol | 2.025 | |
| | | Water | 4.388 | |
| D (Buffer phase) | | Disodium phosphate heptahydrate | 0.0291 | 1.00 |
| | | Mono sodium phosphate monohydrate | 0.0044 | |
| | | Water | 0.9665 | |
| E (Gel phase) | | Carbomer (Ultrez 10) | 0.20 | 7.00 |
| | | Water | 6.8 | |
| F | | Isopropyl alcohol | 0.30 | 0.30 |
| G (pH and adjust) | | Triethanolamine (50% wt/wt aqueous solution) | q.s. | q.s. |
| | | Water | q.s. | |
| | | | | 100.00 |

The components were combined analogously to Example 1.

EXAMPLE 6

A further composition in accordance with the present invention (MC01-17) was prepared by combining the following components:

| Component | | Ingredient | % wt/wt | % wt/wt |
|---|---|---|---|---|
| A (Calcipotriol containing polyaphron) | Oil phase | Calcipotriol base | 0.00447 | 28.125 |
| | | Isopropyl myristate | 18.82 | |
| | | Capric/caprylic triglycerides | 3.375 | |
| | | Laureth-4 | 0.250 | |
| | | Butylated hydroxyanisole | 0.050 | |
| | | α-tocopherol | 0.001 | |
| | Aqueous phase | Calcipotriol | 0.00053 | |
| | | Poloxamer 407 | 0.28 | |
| | | Isopropyl alcohol | 1.70 | |
| | | Water | 3.644 | |
| B (Betamethasone dipropionate containing polyaphron) | Oil phase | Betamethasone dipropionate | 0.0604 | 28.125 |
| | | Isopropyl myristate | 18.82 | |
| | | Capric/caprylic triglycerides | 3.375 | |
| | | Laureth-4 | 0.25 | |
| | | Butylated hydroxyanisole | 0.05 | |
| | | α-tocopherol | 0.001 | |
| | Aqueous phase | Betamethasone dipropionate | 0.004 | |
| | | Poloxamer 407 | 0.28 | |
| | | Isopropyl alcohol | 1.70 | |
| | | Water | 3.5846 | |
| C (Mineral oil polyaphron) | Oil phase | Mineral oil | 26.70 | 34.000 |
| | | Laureth-4 | 0.30 | |
| | Aqueous phase | Cremophor RH40 | 0.34 | |
| | | Methyl parabens | 0.025 | |
| | | Propyl parabens | 0.025 | |
| | | Isopropyl alcohol | 2.000 | |
| | | Water | 4.610 | |

-continued

| Component | Ingredient | % wt/wt | % wt/wt |
|---|---|---|---|
| D (Buffer phase) | Disodium phosphate heptahydrate | 0.0291 | 1.00 |
| | Mono sodium phosphate monohydrate | 0.0044 | |
| | Water | 0.9665 | |
| E (Gel phase) | Carbomer (Ultrez 10) | 0.20 | 7.00 |
| | Isopropyl alcohol | 0.30 | |
| | Water | 6.50 | |
| | Triethanolamine (50% wt/wt aqueous solution) | q.s. to pH 7 | |
| | Water | q.s. | |
| F (pH and adjust) | Triethanolamine (50% wt/wt aqueous solution) | q.s. | q.s. |
| | Water | q.s. | |
| | | | 100.00 |

The polyaphron sub-component A was made by firstly mixing the components of the oil phase together at 40° C. until fully dissolved and then allowed to cool. The aqueous phase components were also mixed with suitable stirring until fully dissolved. The oil phase was then slowly added to the aqueous phase with continuous moderate stirring. After the full oil addition the dispersion was then mixed for a further 30 minutes. The polyaphron sub-components B & C were made using the same method. The buffer phase D was mixed in a separate vessel. In another suitable vessel the gel phase E was made by adding the carbomer to the bulk water with vigorous mixing until fully dispersed and hydrated. The isopropanol was then added and sufficient triethanolamine (50% wt aqueous solution) was added to adjust to pH7.0. Water was then added to make the sub-component up to weight.

The final formulation was then made by mixing the polyaphron sub components (A, B & C) into the gel phase (E) using moderate mixing. This was followed by the addition of the Buffer phase (D). The formulation was then adjusted to pH7.75 using the required amount of triethanolamine 50% wt aqueous solution before being adjusted to 100% wt by the addition of water. The formula was made on a 1 kg scale.

EXAMPLE 7

Variants of MC01-17 were prepared by an analogous method to that of Example 6. The formulae were identical except that they different amounts of TEA were included in component F to achieve different formulation pH values. In particular, formulations having a pH of 7, 7.25, 7.5 7.75 and 8.0 were prepared.

The samples were stored for 9 months at 5° C. in sealed amber glass jars with less than 5% headspace. The jars were sealed in air. The purity (% area) value is calculated from the HPLC trace as the ratio of the API peak to other API related peaks present in the analysis. The results are shown in FIG. 3.

It can be seen from FIG. 3 that the level of the principal calcipotriol degradation product (24-epi calcipotriol) decreases with increasing pH whilst the principal BDP degradation product (betamethasone 21-propionate) increases with increased pH. The calcipotriol degradation was found to increase significantly at pH values below 7.25. The pH range of 7.75±0.5, and preferably 7.75±0.25, was therefore preferred.

EXAMPLE 8

A selection of six formulations including a control were developed with varying solo antioxidants and combinations of them. The samples were stored for 6 months at 40° C. in sealed amber glass jars with less than 5% headspace. The jars were sealed but were not sparged with nitrogen prior to sealing.

The antioxidant is split evenly between the two API oil phases. The antioxidants used were α-tocopherol, butylated hydroxyanisole (BHA), butylated hydroxytoluene (BHT), disodium edetate (EDTA) and citric acid. The levels used for the BHA and BHT were 0.1%. The EDTA was used at 0.05% and the citric acid was used at 0.1%.

| Formulation | |
|---|---|
| MC01-39 | BHA only |
| MC01-40 | α-tocopherol only |
| MC01-41 | BHT only |
| MC01-42 | BHA + α-tocopherol |
| MC01-43 | No antioxidant (control) |
| MC01-46 | BHT + α-tocopherol |

MC01-42 is described in Example 5. The remaining formulations in the table are identical to MC01-42 except for the choice of antioxidant and as indicated above.

Samples were monitored and tested at intervals for pH and API purity.

The calcipotriol purity was determined using the following method:

Chromatographic Conditions

| | |
|---|---|
| HPLC System | Waters Photodiode Array Detector |
| | Waters Separation Module |
| | Waters Empower2 or Empower3 Data Processing Software |
| Column | Phenomenex Kinetex XB C18, 100 × 4.6 mm, 2.6 μm, 00D-4496-E0 |
| Guard Column | SecurityGuard Ultra Cartridges, XB-C18, AJ0-8768 |
| Detection | 266 nm |
| Sample Temperature | 25° C. |
| Column Temperature | 25° C. |
| Flow Rate | 1.0 mL/min |

-continued

| Mobile Phase | Mobile Phase A: Water |  |  |
|---|---|---|---|
|  | Mobile Phase B: Acetonitrile |  |  |
|  | Time (min) | % A | % B |
|  | 0.0 | 90 | 10 |
|  | 25.0 | 10 | 90 |
|  | 30.0 | 10 | 90 |
|  | 30.1 | 90 | 10 |
|  | 35.0 | 90 | 10 |
| Injection Volume | 30 μL |  |  |
| Run Time | 35 min |  |  |

Sample Preparation

Acetonitrile is used as the sample diluent.

Procedure

1. Accurately weigh 0.5 g (±0.025 g) of sample into a 10 ml volumetric flask, minimizing sample on the neck of the flask.
2. Add approximately 5 mL sample diluent to the volumetric flask and vortex mix for 2 minutes.
3. Allow equilibration to room temperature.
4. Make the volumetric flask to volume with sample diluent, add a magnetic stirrer and stir for 2 hours.
5. Transfer the solution to a 20 mL volumetric flask, rinse with washings of heptane and make to volume.
6. Shake for 1 minute and stir for 5 minutes.
7. Transfer an aliquot of the lower layer to a 2 ml centrifuge tube and centrifuge for 10 minutes at 13000 rpm (16,060 g-force).

Standard Preparation

Prepare a Solution of Calcipotriol in Acetonitrile at a Concentration of 2.5 μg/mL 1. Prepare a Calcipotriol stock solution by accurately weight 25 mg Calcipotriol standard into a 250 mL volumetric flask, make to volume with diluent.
2. Prepare an intermediate solution by pipetting 5.0 mL of the stock solution into a 20 mL volumetric flask, making to volume with diluent.
3. Prepare the final standard solution by pipetting 1.0 mL Calcipotriol intermediate solution into a 10 mL volumetric flask, make to volume with diluent.

A suitable equivalent preparation may also be used.

Analysis

Approximate Retention Times:

| Pre-Calcipotriol | 15.9 min |
| Trans Calcipotriol (Imp C) | 16.1 min |
| Calcipotriol | 16.7 min |
| 24-epi Calcipotriol (Imp D) | 17.2 min |

Calculate the Percentage Peak Purity of Calcipotriol using the following equation:

$$\text{Peak Purity (\%)} = \frac{\text{Calcipotriol Peak Area} + \text{Pre-Calcipotroil Peak Area}}{\text{Calcipotriol Peak Area} + \text{Pre-Calcipotroil Peak Area} + \text{Total Calcipotriol Related Impurities Peak Area}}$$

Note: For assay calculations, a response factor of 1.9 is applied to the Pre-Calcipotriol peak area.

The BDP purity was determined using the following method:

Chromatographic Conditions

| HPLC System | Waters Photodiode Array Detector |
|---|---|
|  | Waters Separation Module |
|  | Waters Empower2 or Empower3 |
|  | Data Processing Software |
| Column | Waters Codecs UPLC C18, |
|  | 150 × 2 mm, 1.6 μm |
| Guard Column | Vanguard pre-column, Acquity UPLC BEH |
|  | C18, 2.1 × 5 mm, 1.7 μm (PN 186007096) |
| Detection | 240 nm |
| Sample Temperature | 25° C. (±2° C.) |
| Column Temperature | 40° C. (±2° C.) |
| Flow Rate | 0.28 mL/min |
| Mobile Phase | Mobile Phase A: Water |
|  | Mobile Phase B: 40/60 Methanol/Acetonitrile |

|  | Time (min) | % A | % B |
|---|---|---|---|
|  | 0 | 85 | 15 |
|  | 6.0 | 50 | 50 |
|  | 15.0 | 58 | 42 |
|  | 16.0 | 30 | 70 |
|  | 23.0 | 29 | 71 |
|  | 27.0 | 10 | 90 |
|  | 32.0 | 10 | 90 |
|  | 32.1 | 85 | 15 |
|  | 45 | 85 | 15 |

|  | Column rinse: |
|---|---|
|  | Flush the column for 30 minutes in Acetonitrile/Water 75/25% after use and store in the same solvent |
| Weak wash solvent | Acetonitrile/Water 50/50% (needle wash) |
| Strong wash solvent | Acetonitrile |
| Seal wash solvent | Methanol/Water 10/90% |
| Injection Volume | 4 μL |
| Run Time | 35 min |

Mobile Phases

Mobile Phase A: Rinse the bottle with Acetonitrile before adding water. It is recommended to use an amber bottle and change the water every 5 days, to reduce the growth of bacteria.

Mobile Phase B: Mix Methanol and Acetonitirle in the ratio of 40/60% and sonicate for 10 minutes. Stable for 30 days when stored at ambient temperature.

Sample Preparation

Acetonitrile is used as the sample diluent. Prepare in amber glassware, rinse with acetonitrile before use. Samples are stable for 4 days at ambient conditions.

Procedure:
1. Accurately weigh 1.25 g of sample into a 25 ml volumetric flask, minimizing sample on the neck of the flask.
2. Add approximately 10 mL sample diluent and vortex mix for 1 minute.
3. Sonicate for 5 minutes.
4. Allow to cool to ambient temperature and make to volume with diluent.
5. Add a magnetic stirrer and stir for 2 hours.
6. Leave to stand for 15 minutes.
7. Centrifuge for 10 minutes at 13,000 rpm. Prepare enough vials to allow for filtering.
8. Transfer the solution to a syringe, filter through a 0.2 μm PTFE syringe filter, discarding the first 1 mL.

Standard Preparation

Acetonitrile is used as the sample diluent. Prepare in amber glassware, rinse with acetonitrile before use. Samples are stable for 15 days stored at ambient temperature.

Prepare duplicate solutions of BDP in Acetonitrile at a concentration of 32 μg/mL.

Example Procedure

1. Accurately weigh 25.0 mg (±2 mg) of BDP reference material into a 25 mL flask. Dissolve and dilute to volume with acetonitrile (100 μg/mL stock solution).
2. Pipette 0.8 ml of the stock solution into a 25 mL volumetric flask and dilute to volume with diluent (32 μg/mL working standard solution.)
3. Pipette 1.0 mL of the stock solution into a 100 mL volumetric flask and dilute to volume with diluent (0.32 μg/mL stock sensitivity solution).
4. Pipette 1.0 mL of the stock sensitivity solution into a 10 mL volumetric flask and dilute to volume with diluent (0.032 μg/mL working sensitivity solution, LOQ).
5. Pipette 1.0 mL of the stock sensitivity solution into a 20 mL volumetric flask and dilute to volume with diluent (0.016 μg/mL working sensitivity solution, LOD).

Analysis

Relative Retention Times (RRT's) and Relative response Factors (RRF's):

|  | RRT | RRF |
|---|---|---|
| Betamethasone 17-propionate (Impurity B) | 0.65 | 1.03 |
| E isomer of Enol 21-aldehyde (Impurity E) | 0.76 | 1.05 |
| Betamethasone 21-propionate (Impurity C) | 0.79 | 1.14 |
| Betamethasone 21-Acetate 17-propionate (Impurity D): | 0.95 | 0.98 |
| BHA 1 (not reported) | 0.63 |  |
| BHA 2 (not reported) | 0.65 |  |
| Trans-Calcipotriene (not reported) | 1.03 |  |
| Calcipotriene (not reported) | 1.05 |  |

BDP retention time is approximately 18 minutes.
Calculations:
Inhibit integration between 0-5 minutes and from 25-35 minutes. Disregard peaks due to the placebo, BHA and Calcipotriene.

Calculate the % w/w of the BDP and impurities using the following equation:

$$\text{Assay (\%)} = \frac{\text{Sample area} \times \text{Standard weight (mg)} \times \text{Purity (as a decimal)} \times \text{Dilution Factor (3.2)}}{\text{Standard area} \times \text{Sample weight (mg)} \times RRF}$$

The RRF's of any unknown peak is assumed to be 1.0.
The results for betamethasone dipropionate are shown in the table overleaf.

| Formulation |  | BDP Purity 6 months at 40° C. |
|---|---|---|
| MC01-46 | BHT + α-tocopherol | 95.13 |
| MC01-43 | No antioxidant (control) | 95.16 |
| MC01-41 | BHT only | 95.14 |
| MC01-42 | BHA + α-tocopherol | 95.04 |
| MC01-40 | α-tocopherol only | 95.37 |
| MC01-39 | BHA only | 95.81 |

There appears to be no significant trend or differences with regards to the BDP purity that could not be accounted for by slight changes in pH.

The results for calcipotriol are shown in the table below and in FIG. 4.

| Formulation |  | Calcipotriol Purity 6 months at 40° C. |
|---|---|---|
| MC01-42 | BHA + α-tocopherol | 95.17 |
| MC01-46 | BHT + α-tocopherol | 93.87 |
| MC01-39 | BHA only | 93.31 |
| MC01-41 | BHT only | 92.81 |
| MC01-43 | No antioxidant (control) | 87.2 |
| MC01-40 | α-tocopherol only | 93.53 |

BHA and alpha-tocopherol in combination were found to give significantly improved calcipotriol stability. In contrast, BHA alone, BHT alone, alpha-tocopherol alone and BHT and alpha-tocopherol in combination were found to have similar effects on calcipotriol stability.

EXAMPLE 9

Diffusion experiments were conducted investigating the effect of isopropanol (IPA) level on the amount of calcipotriol and BDP diffused through human skin.

Three formulations were investigated, as summarised in the table overleaf.

| FN ID | IPA level |
|---|---|
| MC01-42 | 5.7% |
| MC01-53 | 0.5% |
| MC01-54 | 0% |

MC01-42 is described in Example 5. The remaining formulations in the table are identical to MC01-42 except for the IPA level as indicated above.

Skin diffusion studies were conducted over 72 hours. For each of the three formulations nine cells were filled with receptor phase (70% phosphate buffer, 30% isopropyl alcohol) and loaded with 30 mg formulation. Receptor phase was collected at 16 h, 24 h, 40 h, 48 h, 64 h and 72 h. Prior to injection into the HPLC all samples and standards were filtered through a PTFE filter (13 mm diameter, 0.45 μm pore size, hydrophilic PTFE, Millipore, UK) to remove paper fibres and other particles from the sample.

A Waters H-Class UPLC system was used for the HPLC analysis. The column used was a BEH C18 50×2.1 mm, 1.7 μm particle size (Waters, UK), fitted with a VanGuard pre-column filter (Waters, UK). The column was maintained at 40° C. throughout. Samples were held at ambient temperature during the analytical run. It was not recommended to chill the samples during the run because buffer salts will precipitate out of the receptor phase matrix.

An isocratic HPLC method was used. Mobile phase of 35/45/20 v/v/v water/acetonitrile/methanol was pumped at 0.5 ml/min. A 10 μl injection volume was used throughout. Detection using a UV-vis photodiode array detector with chromatograms extracted at 240 nm (BDP) and 263 nm (calcipotriene). A run time of 3 min was used. Retention times of 0.9 min (BDP) and 1.3 min (calcipotriene) were observed.

The cumulative amount of the two actives determined at each time-point are summarised in the tables below.

Cumulative Amount Diffused, Calcipotriol Through Human Skin.

| Time (h) | MC01-42 (ng/cm$^2$) | MC01-53 (ng/cm$^2$) | MC01-54 (ng/cm$^2$) |
| --- | --- | --- | --- |
| 16 | 17.5 ± 5.8 | 17.8 ± 1.6 | 32.3 ± 8.7 |
| 24 | 30.6 ± 5.9 | 24.6 ± 5.2 | 20.1 ± 8.2 |
| 40 | 90.2 ± 11.6 | 69.5 ± 12.3 | 57.7 ± 15.6 |
| 48 | 136.4 ± 17.1 | 112.1 ± 15.2 | 86.3 ± 18.4 |
| 64 | 320.2 ± 49.9 | 203.6 ± 30.0 | 149.1 ± 24.3 |
| 72 | 510.3 ± 96.8 | 377.2 ± 44.3 | 203.6 ± 32.0 |

Cumulative Amount Diffused. BDP Through Human Skin.

| Time (h) | MC01-42 (ng/cm$^2$) | MC01-53 (ng/cm$^2$) | MC01-54 (ng/cm$^2$) |
| --- | --- | --- | --- |
| 16 | 123 ± 74 | 47 ± 8 | 136 ± 84 |
| 24 | 253 ± 91 | 142 ± 20 | 203 ± 105 |
| 40 | 758 ± 163 | 368 ± 56 | 521 ± 215 |
| 48 | 1070 ± 202 | 667 ± 66 | 737 ± 227 |
| 64 | 1884 ± 333 | 1132 ± 142 | 1116 ± 270 |
| 72 | 2649 ± 393 | 1569 ± 241 | 1358 ± 289 |

The results are shown graphically in FIGS. 5 and 6.

For both betamethasone dipropionate and calcipotriol, cumulative diffusion at 72 hours was significantly higher when 5.7% isopropanol was included compared to 0.5% and 0%.

EXAMPLE 10

Two variants of MC01-17 (see Example 6) were prepared: one in which a portion of the IPM from each of components A and B was replaced with CCT (to give a total CCT content of 13%), and one in which the CCT was replaced entirely with IPM. MC01-17 itself contained 7% CCT in total.

The human skin diffusion of each of the three formulations was measured using the same method as Example 9. The mean cumulative flux of calcipotriol and BDP in ng/cm$^2$ is shown at different time points in FIGS. 7 and 8 respectively.

As can be seen from FIGS. 7 and 8, the CCT level of 7% shows significantly greater flux (ANOVA) for both calcipotriol (p=0.0015) and BDP (p=0.0162) over the neat IPM (0% CCT) or the 13% CCT. The result is surprising in that it could be thought that the additional IPM, a known permeation enhancer, would be more beneficial but it appears that in this case more is not necessarily better.

A further experiment was carried out in which MC01-17 was compared with the commercially available Dovobet® ointment using the same skin diffusion tests described above. The mean cumulative flux of calcipotriol and BDP in ng/cm$^2$ is shown at different time points in FIGS. 9 and 10 respectively. As can be seen from FIGS. 9 and 10, the skin penetration of both calcipotriol and BDP is surprisingly better for MC01-17 than Dovobet®.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The invention claimed is:

1. A composition for topical application comprising a polyaphron dispersion, the polyaphron dispersion comprising a continuous aqueous phase and at least one discontinuous oil phase,
   wherein the composition comprises, by weight of the composition, from 0.001 to 0.01 wt % calcipotriol, betamethasone dipropionate, from 0.001 to 0.005 wt % alpha-tocopherol, and from 0.05 to 0.5 wt % butylated hydroxyanisole, and
   wherein the composition has a pH of 7.75±0.5.

2. A composition according to claim 1, wherein the composition has a pH of 7.75±0.25.

3. A composition according to claim 1 wherein the composition comprises, by weight of the composition:
   from 0.02 to 0.1 wt % betamethasone.

4. A composition according to claim 1 wherein:
   the at least 60 wt % of the calcipotriol is in at least one of said discontinuous oil phase(s); and/or
   the at least 60 wt % of the betamethasone dipropionate is at least 60 wt % of the betamethasone dipropionate is in at least one of said discontinuous oil phase(s); and/or
   the at least 60 wt % of the alpha-tocopherol is in at least one of said discontinuous oil phase(s); and/or
   the at least 60 wt % of the butylated hydroxyanisole is in at least one of said discontinuous oil phase(s).

5. A composition according to claim 1, wherein at least one of said discontinuous oil phase(s) comprises medium chain triglycerides and isopropyl myristate, wherein the isopropyl myristate and medium chain triglycerides are present in a weight ratio of from 3:1 to 12:1.

6. A composition according to claim 1, wherein the polyaphron dispersion further comprises a discontinuous phase comprising a non-solvent oil.

7. A composition according to claim 1, wherein said discontinuous oil phase(s) comprises a first discontinuous phase, a second discontinuous phase and, optionally a third discontinuous phase comprising mineral oil,
   at least 60 wt % of the calcipotriol is in the first discontinuous phase,
   at least 60 wt % of the betamethasone dipropionate is in the second discontinuous phase, and
   at least 60 wt % of the the alpha-tocopherol and the butylated hydroxyanisole are in the first discontinuous phase, or predominantly in the first and second discontinuous phases collectively.

8. A composition according to claim 7, wherein the first discontinuous phase and the second discontinuous phase each comprise the same pharmaceutically acceptable oil,
   wherein the pharmaceutically acceptable oil is a blend of caprilic capric triglycerides (CCT) and isopropyl myristate, and
   wherein the isopropyl myristate and caprilic capric triglycerides are present in a weight ratio of from 3:1 to 12:1.

9. A composition according to claim 1, wherein the continuous aqueous phase comprises at least 4 wt % isopropanol by weight of the composition.

10. A composition according to claim 1, wherein the composition is chemically stable for at least 6 months at 25° C.±2° C., as measured at 60% RH±5%; and/or
    wherein the composition is chemically stable for at least 12 months at 5° C.±3° C., as measured at 60% RH±5%.

11. A composition according to claim 6, wherein the non-solvent oil comprises mineral oil.

* * * * *

UNITED STATES PATENT AND TRADEMARK OFFICE
CERTIFICATE OF CORRECTION

PATENT NO. : 11,696,919 B2
APPLICATION NO. : 16/982281
DATED : July 11, 2023
INVENTOR(S) : Nigel Crutchley et al.

It is certified that error appears in the above-identified patent and that said Letters Patent is hereby corrected as shown below:

On the Title Page

At page 2, Column 2, Line 1, (Item (56) Other Publications), Delete "Patenatbility" and insert -- Patentability --.
At page 2, Column 2, Line 3, (Item (56) Other Publications), Delete "Patenatbility" and insert -- Patentability --.
At page 3, Column 1, Line 3, (Item (56) Other Publications), Delete "ofErythromycin" and insert -- of Erythromycin --.
At page 3, Column 1, Line 65, (Item (56) (Other Publications), Delete "assessmnet" and insert -- assessment --.
At page 3, Column 2, Line 3, (Item (56) (Other Publications), Delete "CalciptriolBetamethasone" and insert -- CalcipotriolBetamethasone --.
At page 3, Column 2, Line 4, (Item (56) Other Publications), Delete "(DaivobetTM)" and insert -- (Daivobet ™ ) --.
At page 3, Column 2, Line 15, (Item (56) Other Publications), Delete "ofVitamin" and insert -- of Vitamin --.
At page 3, Column 2, Line 18, (Item (56) Other Publications), Delete "Trasdermal" and insert -- Transdermal --.
At page 3, Column 2, Line 22, (Item (56) Other Publications), Delete "vaulgaris:" and insert -- vulgaris: --.
At page 3, Column 2, Line 22, (Item (56) Other Publications), Delete "doubl-blind" and insert -- double-blind --.
At page 3, Column 2, Line 30, (Item (56) Other Publications), Delete "freatment," and insert -- treatment, --.
At page 3, Column 2, Line 55, (Item (56) Other Publications), Delete "Coloids" and insert -- Colloids --.
At page 3, Column 2, Line 69, (Item (56) Other Publications), Delete "Louisianna" and insert -- Louisiana --.
At page 4, Column 2, Line 14, (Item (56) Other Publications), Delete "Storate"," and insert -- Storage", --.

Signed and Sealed this
Nineteenth Day of March, 2024

Katherine Kelly Vidal
*Director of the United States Patent and Trademark Office*

At page 4, Column 2, Line 17, (Item (56) Other Publications), Delete "wiht" and insert -- with --.

In the Specification

At Column 2, Line 64, Delete "fraction)" and insert -- fraction. --.
At Column 3, Line 11, Delete "(6" and insert -- 6 --.
At Column 4, Line 18-19, Delete "Preferably, the composition does not comprise a wax component that is solid at 25° C." and insert the same on Column 4, Line 17, as a continuation of the same paragraph.
At Column 4, Line 20, Delete "caprilic" and insert -- caprylic --.
At Column 4, Line 22, Delete "caprilic" and insert -- caprylic --.
At Column 4, Line 28, Delete "caprilic" and insert -- caprylic --.
At Column 11, Line 52, Delete "caprilic" and insert -- caprylic --.
At Column 11, Line 53, Delete "caprilic" and insert -- caprylic --.
At Column 11, Line 58, Delete "caprilic" and insert -- caprylic --.
At Column 12, Line 8, Delete "caprilic" and insert -- caprylic --.
At Column 12, Line 10, Delete "caprilic" and insert -- caprylic --.
At Column 12, Line 13, Delete "caprilic" and insert -- caprylic --.
At Column 12, Line 15, Delete "caprilic" and insert -- caprylic --.
At Column 12, Line 47, Delete "caprilic" and insert -- caprylic --.
At Column 12, Line 49, Delete "caprilic" and insert -- caprylic --.
At Column 12, Line 52, Delete "caprilic" and insert -- caprylic --.
At Column 12, Line 54, Delete "caprilic" and insert -- caprylic --.
At Column 13, Line 25, Delete "caprilic" and insert -- caprylic --.
At Column 13, Line 27, Delete "caprilic" and insert -- caprylic --.
At Column 13, Line 30, Delete "caprilic" and insert -- caprylic --.
At Column 13, Line 32, Delete "caprilic" and insert -- caprylic --.
At Column 28, Line 5 (Approx.), Delete "Calcipotroil" and insert -- Calcipotriol --.
At Column 28, Line 7 (Approx.), Delete "Calcipotroil" and insert -- Calcipotriol --.
At Column 28, Line 59, Delete "Acetonitirle" and insert -- Acetonitrile --.

In the Claims

At Column 32, Line 43, In Claim 4, after "the" delete "at least 60 wt % of the betamethasone dipropionate is".
At Column 32, Line 66, In Claim 7, delete "the the" and insert -- the --.
At Column 33, Line 7, In Claim 8, delete "caprilic" and insert -- caprylic --.
At Column 33, Line 9, In Claim 8, delete "caprilic" and insert -- caprylic --.